(12) United States Patent
Kulaksiz et al.

(10) Patent No.: US 7,749,713 B2
(45) Date of Patent: Jul. 6, 2010

(54) DIAGNOSTIC METHOD FOR DISEASES BY SCREENING FOR HEPCIDIN IN HUMAN OR ANIMAL TISSUES, BLOOD OR BODY FLUIDS AND THERAPEUTIC USES THEREFOR

(76) Inventors: Hasan Kulaksiz, Steubenstr. 8, Heidelberg (DE); Cyril E. Geacintov, 1061 Belair Ct., Mountainside, NJ (US) 07092; Alfred Janetzko, Scneunenweg 20t, Butzbach/Nieder-Weisel (DE); Wolfgang Stremmel, Ludolf-Krehl-Str. 34, Heidelberg (DE)

( * ) Notice: Subject to any disclaimer, the term of this patent is extended or adjusted under 35 U.S.C. 154(b) by 511 days.

(21) Appl. No.: 10/535,608

(22) PCT Filed: Nov. 19, 2003

(86) PCT No.: PCT/US03/36946

§ 371 (c)(1),
(2), (4) Date: Jan. 6, 2006

(87) PCT Pub. No.: WO2004/058044

PCT Pub. Date: Jul. 15, 2004

(65) Prior Publication Data

US 2007/0134746 A1 Jun. 14, 2007

Related U.S. Application Data

(63) Continuation-in-part of application No. 10/441,089, filed on May 19, 2003, now Pat. No. 7,320,894, which is a continuation-in-part of application No. 10/299,486, filed on Nov. 19, 2002, now Pat. No. 7,411,048.

(51) Int. Cl.
G01N 33/53 (2006.01)
(52) U.S. Cl. .............. 435/7.1; 435/7.92; 435/7.93; 435/7.94; 436/501; 436/512
(58) Field of Classification Search ............ 435/7.1, 435/7.5, 7.92–7.95, 331, 344.1; 436/501, 436/518, 86, 811; 530/387.9, 389.1, 300, 530/350, 387
See application file for complete search history.

(56) References Cited

U.S. PATENT DOCUMENTS

| 5,420,016 | A | 5/1995 | Boguslaski et al. |
| 2002/0091247 | A1 | 7/2002 | Kaser et al. |
| 2003/0027999 | A1 | 2/2003 | Rosen et al. |
| 2004/0234527 | A1 | 11/2004 | Crisanti |
| 2005/0037971 | A1 | 2/2005 | Nicolas et al. |
| 2007/0092916 | A1 | 4/2007 | Kulaksiz et al. |

FOREIGN PATENT DOCUMENTS

| WO | WO00/73454 | 12/2000 |
| WO | WO 00/73454 A1 | 12/2000 |
| WO | WO02/098444 | 12/2002 |

OTHER PUBLICATIONS

Park et al., Hepcidin, a Urinary Antimicrobial Peptide Synthesized in the Liver, The Journal of Biological Chemistry, vol. 276, No. 11, 2001, pp. 7806-7810.*
Kemna et al., Hepcidin from discovery to differential diagnosis, Haematologica 93(1) 2008, pp. 90-97.*
Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
Nemeth et al., "Hepcidin, a putative mediator of anemia of inflammation, is a type II acute-phase protein," Blood (Apr. 1, 2003): vol. 101, No. 7, pp. 2461-2463.
Wild, The Immunoassay Handbook, Stockton Press, 1994, pp. 66.
Diamandis et al, Immunoassay, Academic Press, Chapter 11, The Avidin-Biotin System (1996), pp. 237-255.
Brugnara, Carlo, "Iron deficiency and erythropoiesis: New Diagnostic Approaches," Climincal chemistry 2003; vol. 49, No. 10, pp. 1573-1578.
Swinkles et al., "Hereditary hemochromatosis: genetic complexity and new diagnostic approaches," Clinical chemistry 2006; vol. 52, No. 6, pp. 950-968.
UniProtKB/Swiss-Prot entry Q5U9D2, HEPC CANFA, pp. 1-3, Jun. 28, 2006.
UniProtKB/Swiss-Prot entry P81172, HEPC Human, pp. 1-3, Jun. 28, 2006.
UniProtKB/Swiss-Prot entry Q8MJ80, HEPC Pig, pp. 1-3, Jun. 28, 2006.
UniProtKB/Swiss-Prot entry Q9EQ21, HEPC Mouse, pp. 1-4, Jun. 28, 2006.
Andrews, N. C. (2000) Annu, Rev. Genomics Hum. Genet. 1, 75/98.
Philpott, C.C. (2002) Heatology 35, 993-1001.
Beutler et al., (2001) Drug?Metab. Dispos. 29, 495/499.
Collawn et al., (1990) Cell 63, 1061/1072.

(Continued)

*Primary Examiner*—Melanie Yu
*Assistant Examiner*—Gary W Counts
(74) *Attorney, Agent, or Firm*—Fox Rothschild LLP; Gerard P. Norton; Vyacheslav Vasilyev

(57) ABSTRACT

The present invention concerns methods and kits for diagnosing a disease condition characterized by non-physiological levels of hepcidin protein, including prohepcidin and fragments thereof, comprising obtaining a tissue or fluid sample from a subject; contacting the sample with an antibody or fragment thereof that specifically binds to a polypeptide corresponding to the mid-portion or C terminus of a hepcidin protein, and quantifying the hepcidin level using an assay based on binding of the antibody and the polypeptide; wherein the non-physiological level of hepcidin is indicative of the disease condition. The present invention also concerns diagnostic methods and kits for applications in genetic technological approaches, such as for overexpressing or down-regulating hepcidin. The present invention further concerns therapeutic treatment of certain diseases by treatment of subjects with hepcidin and agonists or antagonists of hepcidin.

3 Claims, 14 Drawing Sheets

OTHER PUBLICATIONS

Kawabata et al., (1999) J. Biol. Chem. 274, 20826-20832.
Camasehella et al., (2000) Nat. Genet. 25, 14-15.
Fleming et al., (2002) Proc. Natl. Acad. Sci. USA 99, 10653/10658.
Fleming et al., (2000) Proc. Natl. Acad. Sci. USA 97, 2214/2219.
Subramaniam et al., (2002) Cell biochem Biophys. 36, 235/239.
Krause et al., (2000) FEBS Lett. 480, 147-150.
Park et al., (2001 J. Biol. Chem. 276, 7806-7810.
Nicholas et al., (2002) Proc. Natl. Acad. Sci. USA 99, 4396-4601.
Pigeon et al., (2001) J. Biol. Chem. 276, 7811-7819.
Nicolas al, (2001) Proc. Natl. Acad. Sci. USA 98, 8780/8785.
Kulaksiz et al., (2002) Proc. Natl. Acad. Sci. USA 99, 6796-6801.
Kulaksiz et al., (2002) Am. J. Pathol. 161, 655-664.
Rost et al., (1999) Hepatology 29, 814-821.
Hunter et al., (2002) J. Biol. Chem., M205305200.
Kawabata et al., (2000) J. Biol. Chem. 275, 16618-16625.
Frazer et al., (2002) Gastroenterology 123, 835-844.
Aden et al., (1979) Nature 282, 615-616.
Schwartz et al., (1985) EMO J. 4, 899-904.
Zhou et al., (1998) Proc. Natl. Acad. Sci. USA 95, 2492-2497.
Levy et al., (1999) Blood 94, 9-11.
Santos et al., (1996) J. Exp. MEd. 184, 1975/1985.
Anderson et al., (2002) Biochem. Soc. Trans. 30, 724-726.
Ravel R., Laboratory Iron Studies, Clinical Laboratory Medicine: Clinical Application of Laboratory Data, 6th Ed. Mosby-Year Book, Inc., 1995, pp. 67 and 605.

Weinstein DA et al., Inappropriate expression of hepcidin is associated with iron refractory anemia: Implications for the anemia of chronic disease, Blood, Nov. 15, 2002, vol. 100, No. 10, pp. 3776-3781; pre-published on Jun. 28, 2002.

Malecki EA et al., Transferrin response in normal and iron-deficient mice heterozygotic for hypotransferrinemia; effects on iron and manganese accumulation, Biometals. Sep. 1998;11(3):265-76.

Craven et al., Tissue distribution and clearance kinetics of non-transferrin-bound iron in the hypotransferrinemic mouse: a rodent model for hemochromatosis, Proc Natl Acad Sci U S A., May 1987; 84(10):3457-61.

Hartman KR et al., Microcytic Anemia With Iron Malabsorption: An Inherited Disorder of Iron Metabolism, American Journal of Hematology, Apr. 1996; 51(4):269-75.

Irwin JJ et al., Anemia in children, Am Fam Physician, Oct. 2001; 64:1379-86.

Fargion S et al., Hereditary hemochromatosis in a patient with congenital dyserythropoietic anemia, Blood, Nov. 15, 2000; 96(10):3653-5.

Goodnough LT et al., Erythropoietin, iron, and erythropoiesis, Blood, Aug. 1, 2000 ;96(3):823-33.

Brill JR et al., Normocytic Anemia, Am Fam Physician, Nov. 15, 2000;62(10):2255-64.

* cited by examiner

Hepcidin Nucleotide Sequence:

```
  1 tcaagaccca gcagtgggac agccagacag acggcacgat ggcactgagc tcccagatct
 61 gggccgcttg cctcctgctc ctcctcctcc tcgccagcct gaccagtggc tctgttttcc
121 cacaacagac gggacaactt gcagagctgc aaccccagga cagagctgga gccagggcca
181 gctggatgcc catgttccag aggcgaagga ggcgagacac ccacttcccc atctgcattt
241 tctgctgcgg ctgctgtcat cgatcaaagt gtgggatgtg ctgcaagacg tagaacctac
301 ctgccctgcc cccgtcccct cccttcctta tttattcctg ctgccccaga acataggtct
361 tggaataaaa tggctggttc ttttgttttc c
```

Hepcidin Amino Acid Sequence

```
  1 malssqiwaa cllllllas  ltsgsvfpqq tgqlaelqpq dragaraswm pmfqrrrrd
 61 thfpicifcc gcchrskcgm cckt
```

FIG. 8
A
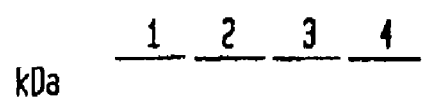
B
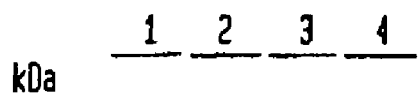
C

FIG. 12
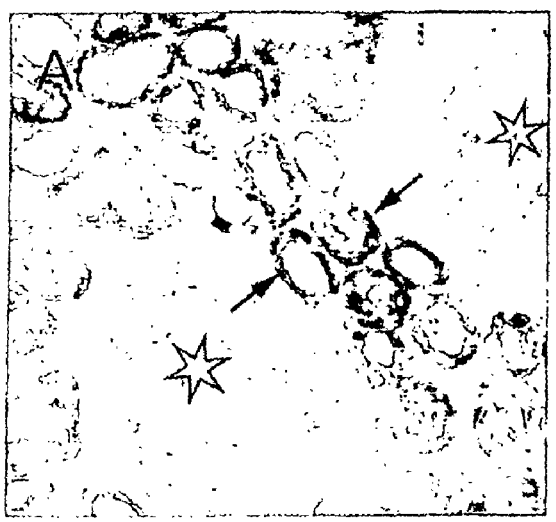
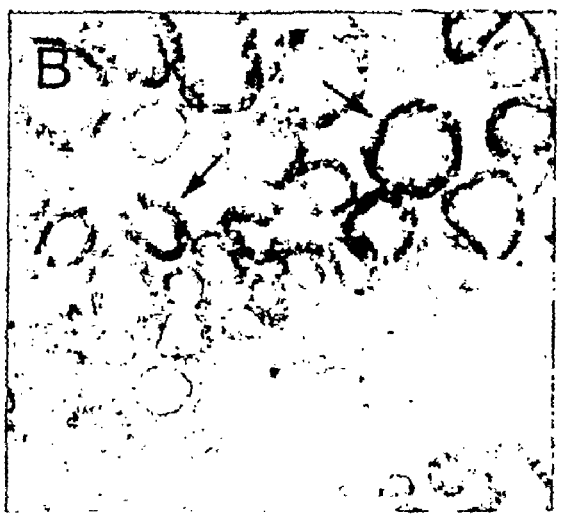
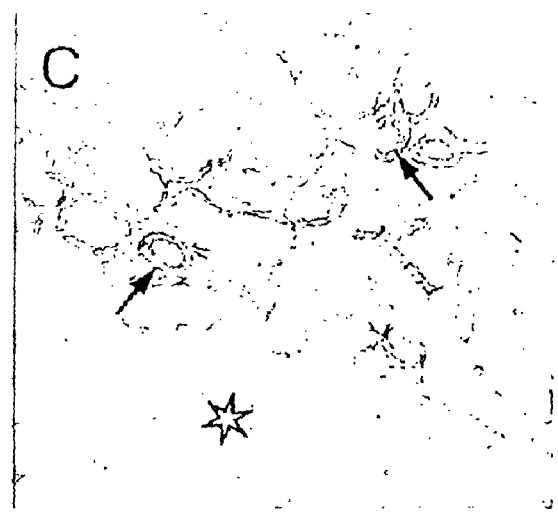
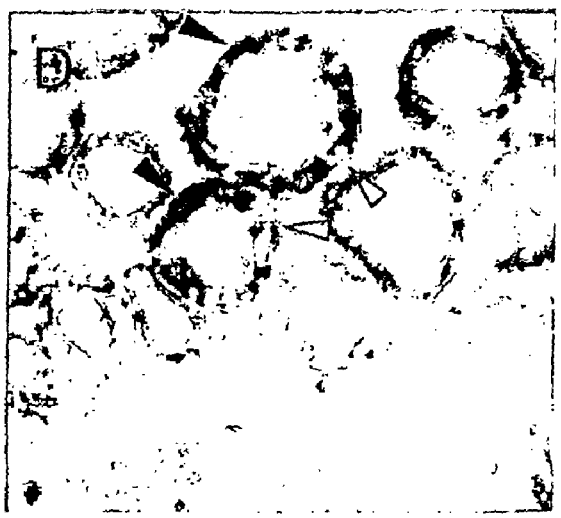

DIAGNOSTIC METHOD FOR DISEASES BY SCREENING FOR HEPCIDIN IN HUMAN OR ANIMAL TISSUES, BLOOD OR BODY FLUIDS AND THERAPEUTIC USES THEREFOR

CROSS-REFERENCE TO RELATED APPLICATIONS

This application claims priority benefits under 35 U.S.C. §371 of PCT International Application No. PCT/US2003/036946 filed Nov. 19, 2003, which is a Continuation-In-Part of application Ser. No. 10/441,089 filed May 19, 2003, now U.S. Pat. No. 7,320,894, and which is a Continuation-In-Part of application Ser. No. 10/299,486 filed Nov. 19, 2002, now U.S. Pat. No. 7,411,048.

BACKGROUND ART

Iron is an essential trace element that is required for growth and development of all living organisms; it is indispensable for DNA synthesis and a broad range of metabolic processes. However, disturbances of iron metabolism have been implicated in a number of significant mammalian diseases, including, but not limited to iron deficiency anemia, hemosiderosis or the iron overload disease hemochromatosis (Pietrangelo, A. (2002) *Am J Physiol. Gastrointest. Liver Physiol.* 282, G403-414; Andrews, N. C. (2000) Annu. Rev. Genomics Hum. Genet. 1, 75-98; Philpott, C. C. (2002) Hepatology 35, 993-1001; Anderson and Powell (2002) Int J Hematol 76, 203-203; Beutler et al., (2001) Drug-Metab. Dispos. 29, 495-499). Under physiological conditions, a human's iron content is regulated by controlling absorption. In mammals, iron absorption occurs predominantly in the duodenum and upper jejunum, and is the only mechanism by which iron stores are physiologically controlled (Philpott, C. C. (2002) *Hepatology* 35, 993-1001). Following absorption, iron is bound to circulating transferrin and delivered to tissues throughout the body. In the liver, the major site of iron storage, transferrin-bound iron is taken into the cells by receptor-mediated endocytosis via the classical transferrin receptor (TfR1) (Collawn et al. (1990) Cell 63, 1061-1072) and presumably in greater amounts via the recently identified homologous transferrin receptor 2 (TfR2) (Kawabata et al. (1999) J Biol Chem 274, 20826-20832). The extracellular domain of this protein is 45% identical to the corresponding portion of TfR1 (Id.). TfR2 can also bind diferric transferrin and facilitate the uptake of iron. Mutations in TfR2 have been associated with certain forms of hemochromatosis demonstrating the important role for TfR2 in iron homeostasis (Philpott, C. C. (2002) Hepatology 35, 993-1001; Camasehella et al., (2000) Nat. Genet. 25, 14-15; Fleming et al., (2002) Proc. Natl. Acad. Sci. USA 99, 10653-10658). TfR2 is predominantly expressed in the liver (Fleming et al., (2000) Proc. Natl. Acadi. Sci. USA 97, 2214-2219; Subramaniam et al., 2002) Cell Biochem. Biophys. 36, 235-239), however, the exact cellular localization is still unknown.

A feedback mechanism exists that enhances iron absorption in individuals who are iron deficient, whereas iron absorption is reduced in persons with iron overload (Pietrangelo, A. (2002) Am J Physiol Gastrointest Liver Physiol 282, G403-414; Philpott, C. C. (2002) Hepatology 35, 993-1001; Anderson and Powell (2002) Int J Hematol 76, 203-203). In hereditary hemochromatosis (HH), however, this regulatory mechanism seems to be impaired; despite iron overload, elevated amounts of iron are absorbed from the diet and lead to accumulation of excess iron in internal organs, resulting in organ dysfunction and failure. The molecular mechanisms by which the intestine responds to alterations in body iron requirements is poorly understood. In this context, hepcidin, a recently identified mammalian peptide (Krause et al. (2000) *FEBS Lett* 489, 147-150; Park et al. (2001) J Biol Chem 276, 7806-7810), is predicted as a key signaling component regulating iron homeostasis (Philpott C. C. (2002) Hepatology 35, 993-1001; Nicolas et al. (2002) Proc Natl Acad Sci USA 99, 4596-4601)

Hepcidin is a small cysteine-rich peptide predominantly produced in the liver. This molecule regulates the absorption of iron in the intestine and inhibits release of iron from macrophages. Hepcidin was initially isolated as an amino acid (aa) peptide in human plasma and urine exhibiting antimicrobial activity (Krause et al. (2000) FEBS Lett 489, 147-150; Park et al. (2001) J Biol Chem 276, 7806-7810). Hepcidin cDNAs encoding an 83 aa precursor in mice and an 84 aa precursor in rat and man, including a putative 24 aa signal peptide, were subsequently identified searching for liver-specific genes that were regulated by iron (Pigeon et al. (2001) J Biol Chem 276, 7811-7819). A cDNA structure for human hepcidin suggests that it is translated as an 84 amino acid prepropeptide that is amino terminally processed to a 60 amino acid residue prohepcidin peptide, which is further processed into a 25 amino acid hepcidin peptide. (Park et al. (2001).

Hepcidin expression is abolished in mice exhibiting iron-overload due to the targeted disruption of upstream stimulatory factor 2 (Usf2) gene resembling the same phenotype as found in hfe−/− mice (Nicolas G, et al (2001) Proc Natl Acad Sd USA 98, 8780-8785), leading to the conclusion that this peptide plays a pivotal role in iron metabolism. In contrast, overexpression of hepcidin was shown to result in severe iron deficiency anemia in transgenic mice (Nicolas et al. (2002) Proc Natl Acad Sci USA 99, 4596-4601), indicating that hepcidin is a central regulator of iron homeostasis. Moreover, recent studies have shown that liver hepcidin expression is decreased in the hfe knockout mouse (Ahmad et al. (2002) Blood Cells Mci Dis 29, 361-366) and mutations in the hepcidin peptide are associated with severe juvenile hemochromatosis (Roetto et al. (2003) Nat Genet 33, 21-22), opening new perspectives in understanding of the molecular pathogenesis of iron overload. However, the mechanism by which hepcidin balances the body iron stores or adjusts the dietary iron absorption in physiologic and pathologic conditions still remains to be identified.

In this respect, the cellular localization of this peptide and its regulation in various iron states are of major importance in the study of hepcidin function. Although Northern blot analysis of human and mouse hepcidin mRNA levels in various organs revealed that hepcidin is predominantly expressed in liver (Krause et al. (2000) FEBS Lett 489, 147-150; Park et al. (2001) J Biol Chem 276, 7806-7810; Nicolas et al. (2002) Proc Natl Acad Sci USA 99, 4596-4601), no data exists on the cellular localization of this peptide.

SUMMARY OF THE INVENTION

The present invention concerns hepcidin regulation of iron uptake by mammalian cells and the use of hepcidin and/or hepcidin specific antibodies in the diagnosis of diseases involving disturbances of iron metabolism. The diagnostic detection kits of the present invention can be particularly useful in screening the overall population of either humans or animals and identifying those subjects who have these diseases.

One aspect of the invention is a method for diagnosing a disease condition characterized by non-physiological levels of hepcidin, comprising obtaining a tissue or fluid sample from a subject; contacting the sample with an antibody or fragment thereof that specifically binds to a polypeptide from the mid-portion (amino acids 20 to 50) or C-terminus (amino acids 65 to 84) of hepcidin of SEQ ID NO: 2, and quantifying the hepcidin level using an assay based on binding of the antibody and the polypeptide; wherein the non-physiological level of hepcidin is indicative of the disease condition. In one aspect of the present invention, sensitive diagnostic methods and kits were established enabling the detection of prohepcidin in human plasma. The invention opens a broad range of therapeutic perspectives, where a hepcidin antibody and diagnostic methods and kits can be used for the determination of hepcidin as a parameter for the progress of the diseases mentioned above during and after therapy.

One embodiment of the invention concerns the generation and purification of a hepcidin protein, including prohepcidin and fragments thereof. Another embodiment of the invention concerns hepcidin specific antibodies, or fragments or variants thereof that, in turn, can be used in immunoassays to detect a hepcidin protein, including prohepcidin in suspected humans or animals.

In another aspect of the invention, the hepcidin diagnostic methods and kits can be used in genetic technological approaches, such as for overexpressing or downregulating hepcidin.

In still another aspect of the invention, hepcidin can be used in therapeutic treatment of the diseases described herein, by treating subjects with hepcidin, and agonists or antagonists of hepcidin. Iron uptake in cells could be modulated by varying the concentration of hepcidin, inhibiting hepcidin binding to iron or to the TfR2 receptor. Accordingly, hepcidin, and agonists or antagonists of hepcidin may be useful in the treatment of conditions where there is a disturbance in iron metabolism. For example, such substances may be useful in the treatment of such aforementioned diseases.

These and other aspects of the present invention will be better appreciated by reference to the following drawings and detailed description.

BRIEF DESCRIPTION OF THE DRAWINGS

FIG. 7 illustrates the complete nucleotide (SEQ ID NO: 1) and amino acid sequences (SEQ ID NO: 2) of one form of hepcidin reproduced from GenBank database accession nos. NN021175 and AAH20612, respectively.

FIG. 8 illustrates as follows: (A) RT-PCR analysis of human (lane 2), mouse (lane 3), and rat (lane 4) kidney showing gene expression of hepcidin. A by DNA ladder is indicated (lanes 1 and 5). (B, C) Western blot analyses of hepcidin in extracts of human lanes 1), rat (lanes 2), and mouse (lanes 3) kidney, as well as in human urine (lanes 4) with antibodies EG(2)-HepN (B), and EG(1)-HepC (C). Note the immunoreactive bands at 9.5 kDa obtained with both antibodies recognizing different epitopes in the hepcidin precursor. (Molecular mass markers used: phosphorylase B, 105 kDa; glutamic dehydrogenase, 53 kDa; carbonic anhydrase, 34 kDa; myoglobin-blue, 23 kDa; myoglobin-red, 17 kDa; lysozyme, 13 kDa; aprotinin, 7 kDa; insulin, 3 kDa)

FIG. 12 illustrates the cellular localization of hepcidin in human kidney. Antibodies EG(1)-HepN (A), EG(2)-HepN (B and D), and EG(1)-HepC (C) show distinct immunoreactivity in distal tubuli of the renal cortex (arrows). In the same tubuli, intercellular differences of hepcidin immunoreactivity exist showing strongly (black arrowheads) and faintly immunoreactive (transparent arrowheads) epithelial cells with cytoplasmic staining. No immunoreactivity is seen in the glomeruli (asterisks). (Magnification: A-C, ×180; D, ×360)

BEST MODE OF CARRYING OUT THE INVENTION

Figure 1:
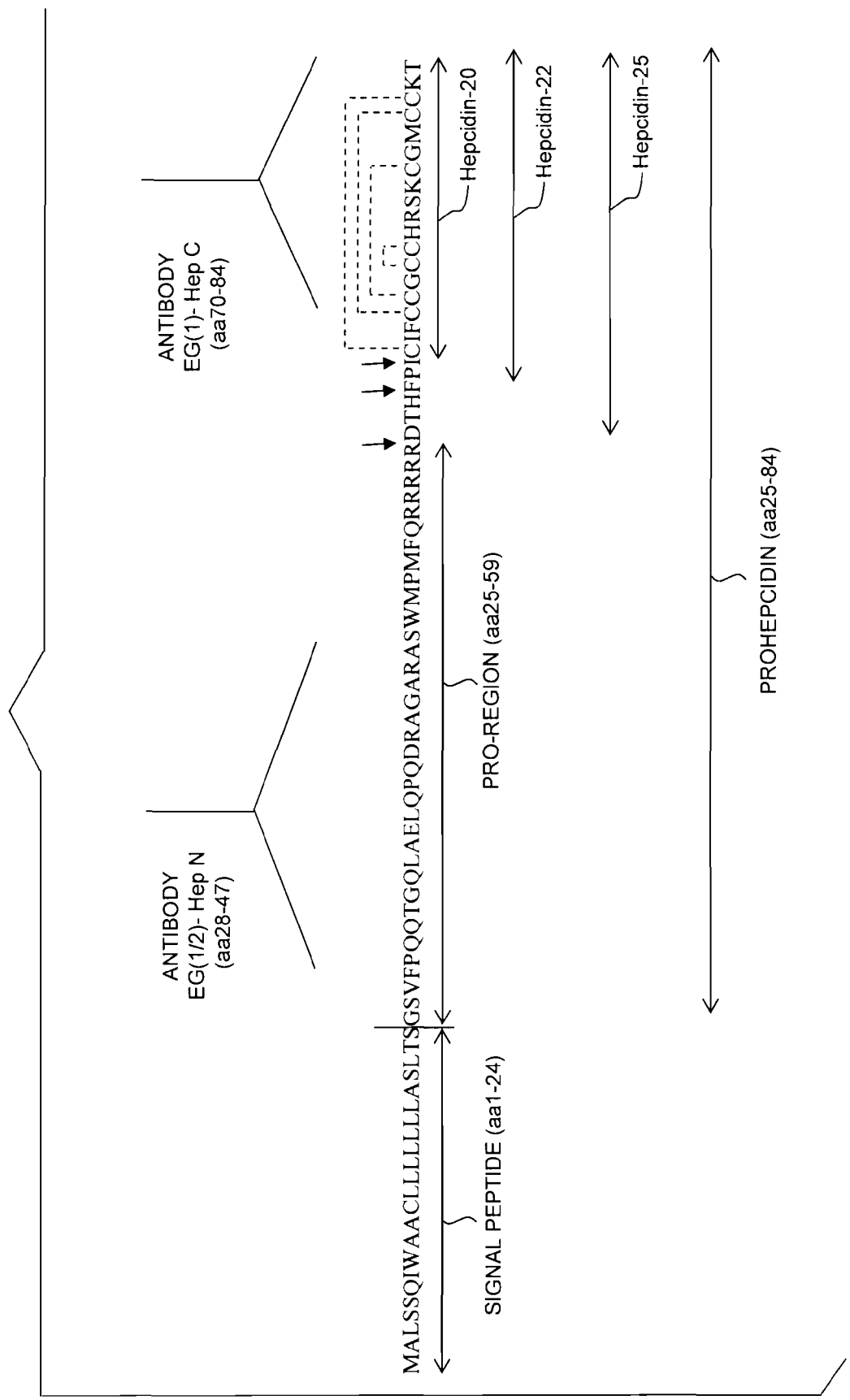
FIG. 1 illustrates the amino-acid sequence of the human hepcidin precursor protein containing a typical 24 aa signal peptide at the N-terminus (the line between aa 24 and 25 indicates the putative signal sequence cleavage site), a 35 aa pro-region, and the C-terminal 20-, 22-, and 25-aa hepcidin peptides differing only by their N-terminal truncation as denoted by arrows. After cleavage of the signal peptide from hepcidin precursor, the prohepcidin molecule is produced consisting of 60 aa. The proposed disulfide connectivity in hepcidin 25 is 1-8, 2-7, 3-6, and 4-5 as shown by dashed lines (from Hunter et al., 20). The antisera EG (1 and 2)-Hep N are raised against hepcidin precursor aa 28-47 (SEQ ID NO: 3), antiserum EG(1)-HepC is raised against aa 70-84 (SEQ ID NO: 4) as denoted by the antibody symbols.
Figure 2A:
FIG. 2 illustrates as follows: (A): RT-PCR analysis of human liver (lanes 2 and 3) and HepG2 cells (lanes 4 and 5) showing gene expression of hepcidin. A by DNA ladder is indicated (lanes 1 and 7). Lane 6 shows a negative control. (B-D): Western blot analyses of hepcidin in extracts of guinea pig (lanes 1) and human liver lanes 2) as well as in HepG2 cells (lanes 3), human serum (lanes 4), and guinea pig skeletal muscle (lanes 5, control) with antibodies EG(1)-HepN (B), EG (2)-HepN (C) and EG (1)-HepC (D). Note the immunoreactive bands at 10 and 20 kDa obtained with all antibodies recognizing different epitopes in the hepcidin precursor. (Molecular mass markers used: phosphorylase B, 105 kDa; glutamic dehydrogenase, 53 kDa; carbonic anhydrase, 34 kDa; myoglobin-blue, 23 kDa; myoglobin-red, 17 kDa; lysozyme, 13 kDa; aprotinin, 7 kDa; insulin, 3 kDa.)
Figure 2B:
Figure 2C:
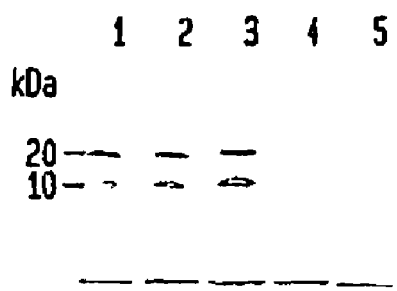
Figure 2D:
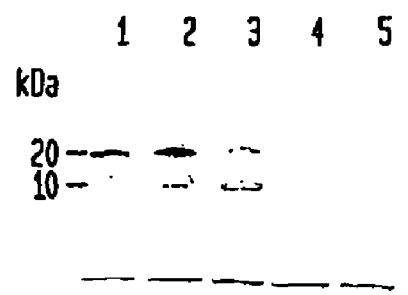

The present invention describes that hepcidin regulates iron uptake by mammalian cells and nonphysiological expression of hepcidin results in disease involved in distribution of iron metabolism. The term hepcidin, as used herein, means prohepcidin, hepcidin or fragments thereof. The physiological concentration of hepcidin in the blood is in the range of about 50 to about 150 ng/ml. Nonphysiological concentrations are below or over this range. Nonphysiological amounts of hepcidin protein or a fragment thereof are associated with disturbances of iron metabolism, resulting in iron deficiency Or overload, such as iron deficiency anemia; genetic and nongenetic iron overload diseases, such as hemosiderosis and hemochromatosis or secondary hemochromatosis, aceruloplasminemia, hypotransferrinemia, atransferrinemia; iron overload diseases of undetermined origin, for instance in the case of diseases of the biliary system, liver diseases, especially alcoholic liver diseases, nonalcoholic steatohepatitis, and chronic hepatitis B and C infections; diseases of utilization of iron, such as sideroblastic anemia, thalassemia; hematologic diseases, such as leukemia, polyglobulie, macrocytic, microcytic or normocytic anemia, anemia with reticulocytosis, hemolytic anemia; disturbances of the reticuloendothelial system due to infections and diseases; inflammations and infections, including sepsis; immunologic diseases and tumors, such as carcinoma, sarcoma, lymphoma, that result in non-physiologic hepcidin concentrations; neurodegenerative diseases, such as Alzheimer's disease and Wilson's disease. This discovery has permitted the development of assays for a hepcidin protein and fragments thereof and their subsequent purification with retention of their native configuration and physiological activity. The invention is based, in part, on the discovery that in patients suffering from certain disorders a hepcidin protein is present in tissue, blood and body fluid of a human or animal.

This invention provides the first demonstration that a hepcidin protein, including prohepcidin in subjects of these disorders are present in human or animal tissue, blood and body fluids in concentrations greatly exceeding that found in normal humans or animals that are not subjects of these disorders. This is achieved by examining a sample of tissue, blood, or body fluid from a patient, and detecting the presence and quantity of hepcidin protein and/or prohepcidin. The detection and quantitative measurement of any hepcidin protein, including prohepcidin or fragment thereof in tissue, blood or body fluids in accordance with this invention is useful in confirming a clinical diagnosis of the diseases described herein, in affected patients and in following the course of the disease. The invention is also useful in monitoring the disease during and subsequent to a period of treatment with agents that are being tested for their ability to stabilize, decrease or prevent the occurrence of such diseases.

For purposes of description only, the invention will be described in terms of: (a) generating a hepcidin protein, including prohepcidin or fragments thereof; (b) generating antibodies that specifically bind a hepcidin protein, including prohepcidin or fragments thereof; (c) diagnostic assays and kits for diagnosing subtyping or monitoring the diseases described herein; (d) methods for over expressing and down regulating hepcidin or prohepcidin; and (e) therapeutic treatment of the diseases described herein.

In one aspect of the invention, Applicants provide a method for determining the role of hepcidin in physiologic conditions and in relevant diseases. In another aspect of the invention Applicants provide specific antibodies against the midportion and the C terminus of the hepcidin precursor molecule. In this aspect of the invention, these antibodies were used to define the cellular localization of hepcidin in the human and guinea pig liver. A sensitive ELISA was established, which detects prohepcidin in human serum of patients with HH, chronic renal insufficiency (CRI) and renal anemia (RA). Applicants have described that prohepcidin is released across the hepatocyte basolateral membrane into the blood and is subjected to renal elimination. Since the serum levels of hepcidin are remarkably downregulated in HH and chronic RA, hepcidin must play a role in the pathophysiology of these diseases.

Production of a Hepcidin Protein Isolating a Hepcidin Protein from Blood and Body Fluids For purposes of the present invention the term hepcidin protein is defined as any mammalian hepcidin polypeptide sharing about 80 percent amino acid sequence identity with the predicted amino acid sequence published by Pigeon and co-workers ((2001) *J. Biol. Chem.* 276, 7811-7819). The hepcidin proteins provided herein include prohepcidin, hepcidin and fragments thereof. The hepcidin proteins provided herein also include proteins characterized by amino acid sequences similar to those of purified hepcidin proteins but into which modification are naturally provided or deliberately engineered. For example, modifications in a hepcidin peptide or DNA sequences can be made by those skilled in the art using known techniques. Modifications of interest in a hepcidin protein sequence may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of a hepcidin protein that are important for the protein function can be determined by various methods known in the art including the alanine-scanning method which involved systematic substitution of single or strings of amino acids with-alanine, followed by testing the resulting alanine-containing variant for biological activity. This type of analysis determines the importance of the substituted amino acid(s) in biological activity.

Production of a hepcidin protein may be accomplished by isolating a hepcidin protein from the tissue, blood or body fluids of humans or animals suffering from hemochromotosis, iron deficiency anemia, hemosiderosis, liver cirrhosis and other such diseases described herein, using standard techniques known by those of skill in the art. Such techniques included in the invention also relate to methods for producing a hepcidin protein comprising growing a culture of host cells in a suitable culture medium, and purifying a hepcidin protein from the cells or the culture in which the cells are grown.

A variety of methodologies known in the art can be utilized to obtain any one of the isolated hepcidin proteins of the present invention. For example, a hepcidin protein can also be produced by chemical synthesis of the amino acid sequence of a hepcidin protein (Pigeon et al., (2001) J. Bid. Chem. 276, 7811-7819), as predicted from the cloning and sequencing of a cDNA coding for a hepcidin protein. This hepcidin protein sequence information may be utilized to predict the appropriate amino sequence of a fragment of a hepcidin protein to be chemically synthesized using standard peptide synthesis methods known in the art. These methods include a solid-phase method devised by R. Bruce Merrifield, (Erickson and Merrifield, "Solid-Phase Peptide Synthesis", in The Proteins, Volume 2, H. Neurath & R. Hill (Eds.) Academic Press, Inc., New York pp. 255-257; Merrifield, (1986) "Solid phase synthesis", Science, 242:341-347). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products. This solid phase method of chemical peptide synthesis can readily be automated making it feasible to routinely synthesize peptides containing about 50 residues in good yield and purity (Stewart and Young, (1984) Solid Phase Peptide Synthesis, 2nd ed., Pierce Chemical Co.; Tam et al., (1983) J. Am. Chem. Soc., 105:6442). For example, a hepcidin protein fragment corresponding to amino acid residues 1 to 50, or 34 to 84 as depicted in FIG. 47 could be synthesized. At the simplest level, commercially available peptide synthesizers are particularly useful in producing small peptides and fragments of a hepcidin protein. Fragments are useful, for example, in generating antibodies against the native hepcidin protein.

One skilled in the art can readily follow known methods for isolating proteins in order to obtain one of the isolated hepcidin proteins/peptides of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-verlag (1994); Sambrook, et al., in Molecular Cloning: A Laboratory Manual; Ausubel et al., Current Protocols in Molecular Biology.

Finally, one or more reverse-phase high performance liquid chromatography (RP-HPLC) steps employing hydrophobic RP-HPLC media, e.g., silica gel having pendant methyl or other aliphatic groups, can be employed to further purify a hepcidin protein. Some or all of the foregoing purification steps, in various combinations, can also be employed to provide a substantially homogeneous isolated recombinant hepcidin protein. A hepcidin protein thus purified is substantially free of other mammalian proteins and is defined in accordance with the present invention as an isolated protein.

The sequence of a hepcidin protein may be identified using the Edman degradation method of protein sequencing. This method sequentially removes one amino acid residue at a time from the amino terminal end of a peptide for subsequent sequence identification by chromatographic procedures. See for example, the techniques described in Konigsberg and Steinman, (1977) Strategy and Methods of Sequence Analysis, in Neurath and Hill (eds.), The Proteins (3rd ed.) Vol. 3, pp. 1-178, Academic Press. In addition, sequence analysis of a hepcidin protein may be accelerated by using an automated liquid phase amino acid sequenator following described techniques (Hewick et al., (1981) J. Biol. Chem., 256:7990-7997; Stein and Undefriend, (1984) Analy. Chem., 136:7-23), thereby allowing for the analysis of picomolar quantities of a hepcidin protein.

The purified hepcidin protein can be used in in vitro binding assays that are well known in the art to identify molecules that bind to a hepcidin protein. These molecules include but are not limited to, for e.g., small molecules, molecules from combinatorial libraries, antibodies or other proteins. The molecules identified in the binding assay are then tested for agonist or antagonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to a tumor or other cell by the specificity of the binding molecule for a hepcidin protein.

Cloning and Expression of Recombinant Hepcidin Protein

In other embodiments, production of a hepcidin protein can be achieved by recombinant DNA technology. For example, appropriate hepcidin nucleotide coding sequences may be synthesized, cloned and expressed in appropriate host cells. Since the DNA sequence coding for a hepcidin protein is known (Pigeon et al., (2001) J. Bid. Chem. 276, 7811-7819), DNA probes may be synthesized by standard methods known in the art to screen cDNA libraries prepared from liver tissue from human or animal subjects suffering from hemochromotosis, iron deficiency anemia, hemosiderosis, liver cirrhosis and other diseases described herein, for specific hepcidin protein cDNA's. These DNA probes can further be used to isolate the entire family of hepcidin protein genes from these cDNA libraries using methods that are well known to those skilled in the art. See, for example, the techniques described in Maniatis et al., (1982) Molecular Cloning A Laboratory Manual, Cold Spring Harbor Laboratory, N.Y., Chapter 7.

Hybridization procedures are useful for the screening of recombinant clones by using labeled mixed synthetic oligonucleotide probes where each probe is potentially the complete complement of a specific DNA sequence in the hybridization sample that includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., (1981) Nucleic Acids Research, 9:879)

Alternatively, an expression library can be screened indirectly for a hepcidin protein of the invention having at least one epitope using antibodies to the protein. Such antibodies can both be polyclonally or monoclonally derived and used to detect an expression product indicative of the presence of a hepcidin protein. Generally, a lambda gt11 library is constructed and screened immunologically according to the method of Huynh, et al., 1985) (in DNA Cloning: A Practical Approach, D. M. Glover, ed., 1:49)

The development of specific DNA sequences encoding a hepcidin protein can also be obtained by: (1) isolation of a double stranded DNA sequence from the genomic DNA, and (2) chemical manufacture of a DNA sequence to provide the necessary codons for the protein of interest.

The polymerase chain reaction (PCR) technique can be utilized to amplify the individual members of a hepcidin family for subsequent cloning and expression of hepcidin protein cDNA5 (e.g., see U.S. Pat. Nos. 4,683,202; 4,683,195; 4,889,818; Gyllensten et al., (1988) Proc. Nat'l Acad. Sci. USA, 85:7652-7656; Ochman et al., (1988) Genetics, 120:621-623; Triglia et al., (1988) Nuci. Acids. Res., 16:8156; Frohman et al., (1988) Proc. Nat'l Acad. Sci. USA, 85:8998-9002; Loh et al., (1989) Science, 243:217-220).

Methods that are well known to those skilled in the art can be used to construct expression vectors containing a hepcidin protein or fragments thereof coding sequences and appropriate transcriptional/translational control signals. These methods include in vitro recombinant DNA techniques, synthetic techniques and in vivo recornbination/genetic recombination. See, for example, the techniques described in Maniatis et al., 1982, Molecular Cloning A Laboratory Manual, Cold Spring Harbor Laboratory, N.Y., Chapter 12.

A variety of host-expression vector systems may be utilized to express a hepcidin protein or fragment thereof. These include but are not limited to microorganisms such as bacteria transformed with recombinant bacteriophage DNA, plasmid DNA or cosmid DNA expression vectors containing a coding sequence for a hepcidin protein or fragments thereof; yeast transformed with recombinant yeast expression vectors containing a coding sequence for a hepcidin protein or fragment thereof; insect cell systems infected with recombinant virus expression vectors (e.g., baculovirus) containing a coding sequence for a hepcidin protein or fragment thereof; or animal cell systems infected with recombinant virus expression vectors (e.g., adenovirus, vaccinia virus) containing a coding sequence for a hepcidin protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a hepcidin protein or fragment thereof.

In yeast, a number of vectors containing constitutive or inducible promoters may be used. For reviews see, Current Protocols in Molecular Biology, Vol. 2, (1988) Ed. Ausubel et al., Greene Publish. Assoc. & Wiley Interscience Ch. 13; Grant et al., (1987) Expression and Secretion Vectors for Yeast, in Methods in Enzymology, Eds. Wu & Grossman, (1987) Acad. Press, N.Y., Vol. 153, pp. 516-544; Glover, (1986) DNA Cloning, Vol. II, IRL Press, Wash., D.C. Ch. 3; and Bitter, (1987) Heterologous Gene Expression in Yeast, Methods in Enzymology, Eds. Berger & Kimmel, Acad. Press, N.Y., Vol. 152, Pp. 673-684; and The Molecular Biology of the Yeast *Saccharomyces*, (1982) Eds. Strathern et al., Cold Spring Harbor Press, Vols. I and II. For complementation assays in yeast, cDNA5 for hepcidin proteins or fragments thereof may be cloned into yeast episomal plasmids (YEp) that replicate autonomously in yeast due to the presence of the yeast 2 mu circle. A hepcidin protein or fragment thereof sequence may be cloned behind either a constitutive yeast promoter such as ADH or LEU2 or an inducible promoter such as GAL (Cloning in Yeast, Ch. 3, R. Rothstein (1986) In DNA Cloning Vol. 11, A Practical Approach, Ed. DM Glover, IRL Press, Wash., D.C.). Constructs may contain the 5' and 3' non-translated regions of a cognate hepcidin protein mRNA or those corresponding to a yeast gene. YEp plasmids transform at high efficiency and the plasmids are extremely stable. Alternatively vectors may be used which promote integration of foreign DNA sequences into the yeast chromosome.

A particularly good expression system that could be used to express a hepcidin protein or fragments thereof is an insect system. In one such system, *Autographa californica* nuclear polyhedrosis virus (AcNPV) is used as a vector to express foreign genes. The virus grows in *Spodoptera frugiperda* cells. A hepcidin protein or fragment thereof coding sequence may be cloned into nonessential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., (1983) J. Biol., 46:586; Smith, U.S. Pat. No. 4,215,051). In addition, materials and methods for baculovirus/insect cell expression systems are commercially available in kit form from, e.g., Invitrogen, San Diego, Calif., U.S.A. (the MaxBat' kit), and such methods are well known in the art, as described in Summers and Smith, Texas Agricultural Experiment Station Bulletin No. 1555 (1987), incorporated herein by reference. As used herein, an insect cell capable of expressing a hepcidin polynucleotide of the present invention is transformed.

In cases where an adenovirus is used as an expression vector, a hepcidin protein or fragment thereof coding sequence may be ligated to an adenovirus transcription/translation control complex, e.g., the late promoter and tripartite leader sequence. This chimeric gene may then be inserted in the adenovirus genome by in vivo or in vitro recombination. Insertion in a non-essential region of the viral genome (e.g., region E1 or E3) will result in a recombinant virus that is viable and capable of expressing a hepcidin protein of fragment thereof in infected hosts. (e.g., See Logan & Shenk, (1984) Proc. Natl. Acad. Sci., (USA) 81:3655-3659). Alternatively, the vaccinia 7.5K promoter may be used. (e.g., see Mackett et al., (1982) Proc. Natl. Acad. Sci., (USA) 79:7415-7419; Mackett et al., (1984) J. Virol., 49:857-864; Panicali et al., (1982) Proc. Natl. Acad. Sci., 79: 4927-4931).

Specific initiation signals may also be required for efficient translation of the inserted hepcidin protein or fragment thereof coding sequences. These signals include the ATG initiation codon and adjacent sequences. In cases where the entire hepcidin protein genome, including its own initiation codon and adjacent sequences, are inserted into the appropriate expression vectors, no additional translational control signals may be needed. However, in cases where only a portion of a hepcidin protein coding sequence is inserted, exogenous translational control signals, including the ATG initiation codon, must be provided. Furthermore, the initiation codon must be in phase with the reading frame of a hepcidin protein or fragment thereof coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., (1987) Methods in Enzymol., 153:516-544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered hepcidin protein or fragment thereof may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

The host cells which contain a hepcidin protein or fragment thereof coding sequence and which express the biologically active hepcidin protein or fragment thereof gene product may be identified by at least four general approaches: (a) DNA-DNA hybridization; (b) the presence or absence of "marker" gene functions; (c) assessing the level of transcription as measured by expression of hepcidin protein mRNA transcripts in host cells; and (d) detection of hepcidin protein gene products as measured by immunoassays or by its biological activity.

In the first approach, the presence of a hepcidin protein or fragment thereof coding sequence inserted in the expression vector can be detected by DNA-DNA hybridization using probes comprising nucleotide sequences that are homologous to a hepcidin protein coding sequence or particular portions thereof substantially as described recently (Pigeon et al., (2001) J. Biol. Chem. 276, 7811-7819)

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if a hepcidin protein or fragment thereof coding sequence is inserted within a marker gene sequence of the vector, recombinants containing a hepcidin protein or fragment thereof coding sequence can be identified by the absence of the marker gene function. Alternatively, a marker gene can be placed in tandem with a hepcidin protein or fragment thereof coding sequence under the control of the same or different promoter used to control the expression of a hepcidin coding sequence. Expression of the marker in response to induction or selection indicates expression of a hepcidin protein coding sequence.

In the third approach, transcriptional activity for a hepcidin protein or fragment thereof coding region can be assessed by hybridization assays. For example, RNA can be isolated and analyzed by Northern blot using a probe homologous to a hepcidin protein or fragment thereof coding sequence or particular portions thereof substantially as described (Pigeon et al., (2001) J. Biol. Chem. 276, 7811-7819). Alternatively, total nucleic acids of the host cell may be extracted and assayed for hybridization to such probes.

In the fourth approach, the expression of a hepcidin protein or fragment thereof product can be assessed immunologically, for example by Western blots, immunoassays such as radioimmunoprecipitation, enzyme-linked immunoassays and the like.

Once a recombinant that expresses a hepcidin protein or fragment thereof is identified, the gene product should be analyzed. This can be achieved by assays based on the physical, immunological or functional properties of the product. For example, the methods of the invention include a process for producing a hepcidin protein in which a host cell containing a suitable expression vector that includes a hepcidin polynucleotide of the invention is cultured under conditions that allow expression of the encoded hepcidin protein. A hepcidin protein can be recovered from the culture, conveniently from the culture medium, or from a lysate prepared from the host cells and further purified. Preferred embodiments include those in which the protein produced by such process is a full length or mature form of the protein.

The present invention further provides isolated hepcidin protein encoded by the nucleic acid fragments of the present invention or by degenerate variants of the nucleic acid fragments of the present invention. By "degenerate variant" is intended nucleotide fragments that differ from a nucleic acid fragment of the present invention (e.g., an ORF) by nucleotide sequence but, due to the degeneracy of the genetic code, encode an identical protein sequence. Preferred nucleic acid fragments of the present invention are the Orbs that encode proteins.

A hepcidin protein of the present invention can alternatively be purified from cells that have been altered to express a hepcidin protein. As used herein, a cell is altered to express a desired polypeptide or protein when the cell, through genetic manipulation, is made to produce a hepcidin protein which it normally does not produce or which the cell normally produces at a lower level. One skilled in the art can readily adapt procedures for introducing and expressing either recombinant or synthetic sequences into eukaryotic or prokaryotic cells in order to generate a cell which produces a hepcidin protein of the present invention.

A hepcidin protein of the invention may also be expressed as a product of transgenic animals, e.g., as a component of the milk of transgenic cows, goats, pigs, or sheep which are characterized by somatic or germ cells containing a nucleotide sequence encoding a hepcidin protein.

A hepcidin protein may also be produced by known conventional chemical synthesis. Methods for constructing a hepcidin protein of the present invention by synthetic means are known to those skilled in the art. The synthetically-constructed hepcidin protein sequences, by virtue of sharing primary, secondary or tertiary structural and/or conformational characteristics with natural hepcidin protein may possess biological properties in common therewith, including protein activity. Thus, they may be employed as biologically active or immunological substitutes for a natural, purified hepcidin protein in screening of therapeutic compounds and in immunological processes for the development of antibodies.

A hepcidin protein of the invention may be prepared by culturing transformed host cells under culture conditions suitable to express the recombinant protein. The resulting expressed hepcidin protein may then be purified from such culture (i.e., from culture medium or cell extracts) using known purification processes, such as gel filtration and ion exchange chromatography. The purification of a hepcidin protein may also include an affinity column containing agents which will bind to the protein; one or more column steps over such affinity resins as concanavalin A agarose, heparin-toyopearl or Cibacrom blue 3GA Sepharose one or more steps involving hydrophobic interaction chromatography using such resins as phenyl ether, butyl ether, or propyl ether; or immunoaffinity chromatography.

Alternatively, a hepcidin protein of the invention may also be expressed in a form that will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. A hepcidin protein can also be tagged with an epitope and subsequently purified by using a specific antibody directed to such epitope. One such epitope ("FLAG®") is commercially available from Kodak (New Haven, Conn.).

Other fragments and derivatives of the sequences of hepcidin proteins/peptides which would be expected to retain protein activity in whole or in part (e.g., binding to a TfR2 receptor, binding to a hepcidin specific antibody, etc.) and are useful for screening or other immunological methodologies may also be easily made by those skilled in the art given the disclosures herein. Such modifications are encompassed by the present invention.

A hepcidin protein or fragment thereof should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

Generation of Antibodies which Define a Hepcidin Protein or Fragment Thereof

Various procedures known in the art may be used for the production of antibodies to the mid-portion (amino acids 20 to 50) or C-terminus of epitopes (amino acids 65 to 84) of a hepcidin protein of SEQ ID NO: 2. The hepcidin specific antibodies bind those epitopes and no other known sequences. Such antibodies include but are not limited to polyclonal, monoclonal, chimeric, single chain, Fab fragments and an Fab expression library. For the production of antibodies, various host animals may be immunized by injection with a particular hepcidin protein, or a synthetic hepcidin protein, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*.

Polyclonal antibodies may be readily generated by one of ordinary skill in the art from a variety of warm-blooded animals such as horses, cows, various fowl, rabbits, mice, or rats. Briefly, hepcidin is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to hepcidin. Particularly preferred polyclonal antisera will give a signal on one of these assays that is at least three times greater than background. Once the titer of the animal has reached a plateau in terms of its reactivity to hepcidin, larger quantities of antisera may be readily obtained either by weekly bleedings, or by exsanguinating the animal.

Monoclonal antibodies to peptides of hepcidin may be prepared by using any technique that provides for the production of antibody molecules by continuous cell lines in culture. These include but are not limited to the hybridoma technique originally described by Kohier and Milstein, (Nature, (1975) 256:495-497), the more recent human B-cell hybridoma technique (Kosbor et al., (1983) Immunology Today, 4:72) and the EBV-hybridoma technique (Cole et al., (1985) Monoclonal Antibodies and Cancer Therapy, Alan R. Liss, Inc., pp. 77-96). In an additional embodiment of the invention monoclonal antibodies specific to hepcidin proteins/peptides may be produced in germ-free animals utilizing recent technology (PCT/US90/02545). According to the invention, human antibodies may be used and can be obtained by using human hybridotnas (Cote at al., (1983) Proc. Natl. Acad. Sci., 80:2026-2030) or by transforming human B cells with EBV virus in vitro (Cole et al., (1985) in, Monoclonal Antibodies and Cancer Therapy, Alan R. Liss, pp. 77-96). In fact, according to the invention, techniques developed for the production of "chimeric antibodies" (Morrison et al., (1984) Proc. Natl. Acad. Sci., 8 1:6851-6855; Neuberger et al., (1984) Nature, 312:604-608; Takeda et al., (1985) Nature, 314:452-454) by splicing the genes from a mouse antibody molecule of appropriate antigen specificity together with genes from a human antibody molecule of appropriate biological activity can be used; such antibodies are due to this invention.

According to the invention, techniques described for the production of single chain antibodies (U.S. Pat. No. 4,946,778) can be adapted to produce hepcidin protein-specific single chain antibodies.

An additional embodiment of the invention utilizes the techniques described for the construction of Fab expression libraries (Huse et al., (1989) Science, 246:1275-1281) to allow rapid and easy identification of monoclonal Fab fragments with the desired specificity to hepcidin proteins/peptides.

Antibody fragments that contain specific binding sites for a hepcidin protein may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Diagnostic Assays and Kits

Yet another purpose of the present invention is to provide reagents for use in diagnostic assays for the detection of a hepcidin protein from individuals suffering from hemochromotosis, iron deficiency anemia, hemosiderosis, liver cirrhosis and such other diseases described herein.

In one mode of this embodiment, a hepcidin protein of the present invention may be used as an antigen in immunoassays for the detection of those individuals suffering from hemochromotosis, iron deficiency anemia, hemosiderosis, liver cirrhosis and such other diseases described herein. A hepcidin protein, polypeptide and/or peptide of the present invention may be used in any immunoassay system known in the art including, but not limited to: radioimmunoassays, enzyme-linked immunosorbent assay, "sandwich" assays, precipitin reactions, gel diffusion immunodiffusion assays, agglutination assays, fluorescent immunoassays, protein A immunoassays and immunoelectrophoresis assays, to name but a few. U.S. Pat. No. 4,629,783 and patents cited therein also describe suitable assays.

According to the present invention, monoclonal or polyclonal antibodies produced to various forms of a hepcidin protein, can be used in an immunoassay on samples of blood, spinal fluid or other body fluid to diagnose subjects with hemochromotosis, iron deficiency anemia, hemosiderosis, liver cirrhosis and other diseases described herein.

In one embodiment of the invention, a sample of blood is removed from the patient by venesection and placed in contact with an anticoagulant such as EDTA, mixed, centrifuged at 600 g for 10 min and the plasma removed as is common in the art or a sample of spinal fluid is removed from the patient by lumbar puncture.

The antibodies described herein may be used as the basic reagents in a number of different immunoassays to determine the presence of a hepcidin protein in a sample of tissue, blood or body fluid. Generally speaking, the antibodies can be employed in any type of immunoassay, whether qualitative or quantitative. This includes both the two-site sandwich assay and the single site immunoassay of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention.

For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labelled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labelled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for a hepcidin protein. Thus, a number of possible combinations are possible.

As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid containing a hepcidin protein to be tested is then added to the solid phase complex and incubated at 25° C. for a period of time sufficient to allow binding of any hepcidin protein present to the antibody specific for hepcidin protein. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, β-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labelled antibody is added to the first antibody-hepcidin protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Alternately, fluorescent compounds, such as fluorescein or rhodamine, may be chemically coupled to antibodies without altering their binding capacity. When activated by illumination with light of a particular wavelength, the fluorochrome-labelled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antibody-hepcidin protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Alternatively, the sample to be tested either human blood or spinal fluid containing a hepcidin protein may be used in a single site immunoassay wherein it is adhered to a solid substrate either covalently or noncovalently. An unlabeled anti-hepcidin protein antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for a hepcidin protein of interest.

A hepcidin gene (mutated or normal) can be utilized in an assay of iron metabolism. The gene is expressed, with or without any accompanying molecules, in cell lines or primary cells derived from human or animal subjects, healthy subjects, or cells from other organisms (such as rodents, insects, bacteria, amphibians, etc.). Uptake of iron by these cells is measured, for example through the use of radioactive isotopes. Further, binding of iron to a hepcidin gene product can also be measured. Such experiments assist in assessing the role of a hepcidin gene and hepcidin gene product in iron uptake, binding, and transport by and in cells.

Therapeutic Treatment

In one aspect of the invention, the hepcidin diagnostic methods and kits can be used in genetic technological approaches, such as for over expressing or down regulating hepcidin. In certain therapeutic applications, it is desirable to down regulate the expression and/or function of a hepcidin gene, a mutant hepcidin gene, a hepcidin protein, or a mutant hepcidin protein. For example, down regulation of a normal hepcidin gene or a normal hepcidin protein is desirable in situations where iron is under accumulated in the body, for example in certain anemias (i.e., thalassaemias, hemolytic anemias, transfusions). On the other hand, down regulation of a mutant hepcidin gene or a hepcidin protein is desirable in situations where iron is over accumulated in the body.

As discussed above antibodies specific to a normal or a mutant hepcidin protein can be prepared. Such antibodies can be used therapeutically in the diseases described herein. For example, to block the action of a mutant or normal hepcidin gene if the function associated with a mutant protein is an up regulation of a normal hepcidin protein function and leads to an over accumulation of iron in the body. Similarly, antibodies can be used therapeutically to block action of a hepcidin protein that is causing an under accumulation of iron in the body.

In a similar manner, a hepcidin gene, either in a normal or in a mutant form, can be down regulated through the use of antisense oligonucleotides directed against the gene or its transcripts. A similar strategy can be utilized as discussed above in connection with antibodies. For a particularly valuable review of the design considerations and use of antisense oligonucleotides, see Uhlmann et al., (1990) Chemical Reviews 90:543-584, the disclosure of which is hereby incorporated by reference. The antisense oligonucleotides of the present invention may be synthesized by any of the known chemical oligonucleotide synthesis methods. Such methods are generally described, for example, in Winnacker Chirurg (1992) 63:145. Antisense oligonucleotides are most advantageously prepared by utilizing any of the commercially available, automated nucleic acid synthesizers. One such device, the Applied Biosystems 380B DNA Synthesizer, utilizes beta-cyanoethyl phosphoramidite chemistry.

Since the complete nucleotide synthesis of DNA complementary to a hepcidin gene is known, the mRNA transcript of the cDNA sequence is also known. As such, antisense oligonucleotides hybridizable with any portion of such transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12-40 nucleotides are preferred, more preferably 15-30 nucleotides, most preferably 18-26 nucleotides. Sequences of 18-24 nucleotides are most particularly preferred.

In still another aspect of the invention, hepcidin can be used in the therapy of the disorders described herein, by treating subjects with hepcidin, and agonists or antagonists of hepcidin. Iron uptake in cells can be modulated by varying the concentration of hepcidin, and/or inhibiting hepcidin binding to iron or to the transferrin receptor. Accordingly, hepcidin, and agonists or antagonists of hepcidin may be useful in the treatment of conditions where there is a disturbance in iron metabolism. For example, such substances may be useful in the treatment of conditions such as haemochromatosis, neurodegenerative diseases, ischemic tissue damage, including ischemic stroke or trauma, heart disease, and tumors, in particular skin cancer and such other diseases described herein.

The invention also contemplates methods of modulating iron metabolism using hepcidin. In particular, the present invention relates to a method for treating conditions involving disturbances in iron metabolism comprising administering an iron-modulating amount of hepcidin, or a stimulant, agonist or antagonist of hepcidin. Conditions involving disturbances in iron metabolism which may be treated using the method of the invention include by way of example haemochromatosis, neurodegenerative diseases, ischemic tissue damage, including ischemic stroke or trauma, heart disease, and tumors, in particular skin cancer and such other diseases described herein. A substance which is an agonist or antagonist of hepcidin may be identified by determining the effect of the substance on the binding activity of hepcidin and iron, or hepcidin and the transferrin receptors TfR1 or TfR2, or the effect of the substance on the expression of hepcidin in cells capable of expressing hepcidin including cells genetically engineered to express hepcidin on their surface.

The invention therefore in one aspect relates to a method of identifying agonists or antagonists of hepcidin comprising reacting a substance suspected of being an agonist or antagonist of hepcidin with hepcidin and iron under conditions such that hepcidin is capable of binding to iron; measuring the amount of hepcidin bound to iron; and determining the effect of the substance by comparing the amount of hepcidin bound to iron with an amount determined for a control.

The invention also relates to a method of identifying agonists or antagonists of hepcidin comprising reacting a substance suspected of being an agonist or antagonist of hepcidin with hepcidin and transferrin receptor under conditions such that hepcidin is capable of binding to the transferrin receptor; measuring the amount of hepcidin bound to a transferrin receptor; and determining the effect of the substance by comparing the amount of hepcidin bound to a transferrin receptor with an amount determined for a control. The invention also relates to a method of identifying agonists or antagonists of hepcidin comprising reacting a substance suspected of being an agonist or antagonist of hepcidin with a cell which produces hepcidin, measuring the amount of hepcidin expressed by the cell, and determining the effect of the substance by comparing the amount of expression of hepcidin with an amount determined for a control. The invention further relates to a method for identifying an agonist or antagonist of hepcidinmediated iron uptake comprising: incubating a cell expressing hepcidin on its surface and a substance suspected of being an agonist or antagonist of hepcidin in the presence of iron and in the absence of transferrin, measuring the amount of iron uptake into the cell, and identifying an agonist or antagonist of hepcidin-mediated iron uptake by comparing the amount of iron uptake in the cell with the amount of iron uptake in a cell from a control incubation in the absence of the substance.

In some embodiments of the invention, hepcidin peptides are provided for therapeutic use in subjects having symptoms of a primary iron overload disease or syndrome, such as hemochromatosis, or other iron overload condition caused by secondary causes, such as repeated transfusions. A hepcidin peptide can be full-length hepcidin or some fragment of hepcidin. Preferably, a hepcidin peptide comprises the amino acid residues 28 to 47 or 70 to 80 of a hepcidin (SEQ ID NO: 2). The predicted amino acid sequence and genomic and cDNA sequences of hepcidin were provided in (Krause et al., (2000) FEBS Lett. 480, 147-150; Pigeon et al., (2001) J. Biol. Chem. 276, 7811-7819), hereby incorporated by reference in their entirety. A hepcidin protein or fragment thereof may be administered with beta-2-microglobulin, such as in the form of a complex. In some embodiments, a hepcidin protein greater than about 20 amino acids is administered in a complex with beta-2-microglobulin.

In some embodiments of the invention, agonists or antagonists of a hepcidin protein or a transferrin receptor are provided. Agonists of a hepcidin polypeptide, and/or antagonists of a transferrin receptor, are useful for example, in the treatment of primary or secondary iron overload diseases or syndromes, while antagonists of a hepcidin polypeptide, or agonists of the transferrin receptor are useful, for example, in the treatment of iron deficiency conditions, such as anemias. In other embodiments, mutant hepcidin proteins/peptides are provided which function as antagonists of the wild-type hepcidin protein. Antagonists or agonists can also be antibodies, directed against a transferrin receptor, or the mid-portion (amino acids 20 to 50) or C-terminal region (amino acids 65 to 84) of a hepcidin protein (SEQ ID NO: 2). In some embodiments of the invention, hepcidin polypeptides can serve as antagonists of a transferrin receptor. In further embodiments of the invention, peptidomimetics can be designed using techniques well known in the art as antagonists or agonists of a hepcidin protein and/or a transferrin receptor.

Ligands for a transferrin receptor, whether antagonists or agonists, can be screened using the techniques described herein for the ability to bind to a transferrin receptor. Additionally, competition for hepcidin binding to a transferrin receptor can be done using techniques well known in the art. Ligands, or more generally, binding partners for a hepcidin protein can be screened, for example, for the ability to inhibit the complexing of a hepcidin polypeptide to beta-2-microglobulin, using techniques described herein.

In some embodiments of the invention, agonists or antagonists of transferrin are similarly utilized to increase or decrease the amount of iron transported into a cell, such as into a patient's hepatocytes or lymphocytes. For example, the efficacy of a drug, therapeutic agent, agonist, or antagonist can be identified in a screening program in which modulation is monitored in in vitro cell systems. Host cell systems that express various mutant hepcidin proteins/peptides and are suited for use as primary screening systems. Candidate drugs can be evaluated by incubation with these cells and measuring cellular functions dependent on a hepcidin gene or by measuring proper hepcidin protein folding or processing. Such assays might also entail measuring receptor-like activity, iron transport and metabolism, gene transcription or other upstream or downstream biological function as dictated by studies of hepcidin gene function.

Alternatively, cell-free systems can be utilized. Purified hepcidin protein can be reconstituted into artificial membranes or vesicles and drugs screened in a cell-free system. Such systems are often more convenient and are inherently more amenable to high throughput types of screening and automation.

Criteria for the determination of the purity of a hepcidin protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

In some embodiments of the invention, drugs can be designed to modulate a hepcidin gene and a hepcidin protein activity from knowledge of the structure and function correlations of a known hepcidin protein. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures that can interact with and modify a hepcidin protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semisolid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The invention is not limited to the embodiments described herein and may be modified or varied without departing from the scope of the invention.

EXAMPLES

Example 1

Expression of Hepcidin in the Human Liver Tissues and Tissue Preparation

Human liver samples (n=7) used in the present study were obtained after hemi-hepatectomy in adult subjects with liver metastases. Healthy tissues were fixed in 4% paraformaldehyde for immunohistochemistry or immediately frozen in liquid nitrogen for RT PCR, Western blot and immunofluorescence analysis.

Guinea pigs (n=7) and mice (n=S) were anesthetized and subsequently sacrificed by cervical dislocation. Tissue specimens from liver, skeletal muscle and heart were resected and immediately frozen in liquid nitrogen for Western blot analysis or fixed in paraformaldehyde.

Peptide Synthesis, Immunization Procedure, and Antibodies.

From the published prohepcidin sequence (Krause et al., (2000) FEBS Lett. 480, 147-150; Pigeon et al., (2001) J. Bid. Chem. 276, 7811-7819), the peptides hepcidin-(28-47) and hepcidin-(70-84) were synthesized as C terminal amides using a standard Fmoc protocol (Cetin et al., (1994), Proc. Natl. Acad. Sci. USA 91, 2935-2939). Peptides were coupled to keyhole limpet hemocyanin using m-maleimidobenzoyl-N-hydroxysuccinimide ester, and two SPF rabbits (Charles River If fa Credo) were immunized with each peptide conjugate (Eurogentec, Seraing, Belgium). After testing the titer by ELISA, three antisera [EG(1)-HepC directed against hepcidin(70-84) and EG(1)-HepN and EG(2)-HepN, each directed against hepcidin-(28-47) were used in the present study (FIG. 1) (hepcidin 28-47: PQQ TGQ LAE LQP QDR AGA RA SEQ. (SEQ ID NO: 3), hepcidin 70-84: CGC CHR SKC GMC CKT (SEQ ID NO: 4)). The peptide epitopes used for the generation of the antisera displayed no homology to any hitherto reported protein as confirmed by the BLAST P2 search.

The BT-TFR21 S antibody against mouse TfR2 (BioTrend, Cologne, Germany) was raised against the cytoplasmic N-terminus of mouse TfR2-alpha (TfR2) is alternatively spliced to alpha and beta isoforms, see Fleming et al., (2000) Proc. Natl. Acad. Sci. USA 97, 2214-2219), showing 68% sequence homology to the corresponding region of human TfR2-alpha. The antibody was generated in rabbits and affinity purified.

Expression Analyses in the Human Liver.

RNA isolation was performed using Qiagen RNA easy kit including DNA digestion. Reverse transcription (RT)-PCR analysis was performed as described previously (Kulaksiz et al., (2002) Proc. Natl. Acad. Sci. USA 99, 6796-6801; Kulaksiz et al., (2002) Am. J. Pathol. 161, 655-664) using the following primers and specifications given in 5-3' orientation: human hepcidin (GenBank database accession no. NM0211175), 5'-CTG CAA CCC CAG GAC AGA G-3' (SEQ ID NO: 5) and 5, GGA ATA AAT AAG GAA GGG AGG GG-3', (SEQ ID NO: 6) corresponding to nucleotide positions 147-165 and 338-316. Human TfR2 (#AFO6 7864), 5'-GAT TCA GGG TCA GGG AGG TG-3' (SEQ ID NO: 7) and 5'-(GAA GGG GCT GTG ATT GAA GG-3' (SEQ ID NO: 8); corresponding to nucleotide positions 2496-2515 and 2694-2675. After an initial denaturation of 94° C. for 4 min; reactions were subjected to 35 cycles of the following thermal program: 94° C. for 30 s, 60° C. for 30 s, and 72° C. for 30 s; this program was followed by a final 5 min elongation step at 72° C. Amplification products were run on an ethidium bromide-stained 1.8% 89 mM Tris/89 mM boric acid/2 mM EDTA (pH 8.3) agarose gel. The amplification of significant levels of genomic DNA was excluded by appropriate controls.

Expression Analyses in HepG2 Cells.

The human hepatoma HepG2 cells were obtained from the German Collection of Microorganisms and Cell Culture (Braunschweig, Germany) and grown at 37° C. in 5% $CO_2$ in RPMI 1640 media (Gibco, Karisruhe, Germany) supplemented with 10% (vol/vol) heat-inactivated FBS, penicillin (100 units/ml), and streptomycin (100 mg/ml). Cells were analyzed by RT PCR using the primer specifications mentioned above. For immunofluorescence microscopy, HepG2 cells were grown on glass slides fixed for 4 min in methanol, and pertneabilized with 0.5% Triton X-100 in PBS. After incubation with hepcidin (1:2000) and TfR2 antibodies (1:1000) for 60 min, followed by incubation with Cy-3-conjugated anti-rabbit antibody (Dianova, Hamburg, Germany), the immunostaining was investigated under an Olympus AX70 microscope using appropriate filters.

Extraction of Hepcidin and TfR2 from Serum, Tissues and HepG2 Cells.

As a larger source of hepcidin Applicants used serum collected from patients with chronic renal failure. For extraction of hepcidin, 20 ml serum samples were diluted 1:1 with 0.01 N HCl and adjusted to pH 3.0 with concentrated HCl. Frozen tissues and HepG2 cells were mixed in 0.5 M acetic acid and boiled for 8 min as described (Cetin et al. (1994) Proc Natl Acad Sci USA 91, 2935-2939; Cetin et al. (1995) Proc Natl Acad Sd USA 92, 5925-5929) After homogenization with an Ultra-Turrax homogenizer (Janke & Kunkei, Staufen, Germany) the samples were centrifuged at 20,000×g for 20 min at 4° C. and the supernatants were filtered through a 0.45-μm pore size filter. To enrich proteins, serum samples, cell and total tissue extracts were applied to an octadecasilyl (C18) Sep-Pak cartridge (Waters, Mass.). The column was washed with 0.01 M HCl and eluted with 30% (vol/vol) 2-propanol/30% (vol/vol) methanol/0.01 M HCl (Cetin et al. (1994) Proc Natl Acad Sci USA 91, 2935-2939). Protein fractions were lyophilized and stored at 800 C until use. For TfR2 analysis, tissues and cells were homogenized in Tris-HCl buffer containing 100 mM NaCl, 50 mM Tris-HCl, pH 7.4, 10% glycerol, 1% Triton X-100, 2 mg/ml leupeptin, 2 mg/ml pepstatin, and 1 mM phenylmethylsulfonyl fluoride, and centrifuged at 100,000 g for 30 min at 4° C.

Immunoblot Analysis.

For Western blot analysis, protein extracts were incubated for 7 min at 94° C. in sample buffer with 4% (wt/vol) SDS (Merck, Darmstadt, Germany), 50 mM Tris-HCl (pH 8.15), 1 mM EDTA, 3.24 mM dithiothreitol (Roth, Karisruhe, Germany), 12.5% (wt/vol) glycerol (Merck), and 0.002% bromophenol blue (Merck). To detect hepcidin, a 16.5% tricine-SDS-polyacrylamide gel was used according to the protocols published (Cetin et al., (1994), Proc. Natl. Acad. Sci. USA 91, 2935-2939; Kulaksiz et al., (2002) Proc. Natl. Acad. Sd. USA 99, 6796-6801; Kulaksiz et al., (2002) Am. J. Pathol. 161, 655-664; Cetin et al., (1995) Proc. Natl. Acad. Sci. USA 92, 5925-5929.) TfR2 immunoblots were performed using 8% SDS-polyacrylamide gels. Following electrophoresis, proteins were transferred onto hydrophobic polyvinylidene fluoride-based membranes (Pall, Portsmouth, England) by semi-dry blotting. The membranes were incubated overnight with hepcidin or TfR2 antibodies at dilutions mentioned above. After washing in Tris-buffered saline containing 10 mM Tris-HCl (pH 8.0), 150 mM NaCl, and 0.05% Tween 20, the respective immunoreactive proteins were visualized after incubation with alkaline phosphatase-conjugated goat anti-rabbit antibody (diluted 1:50,000; Sigma) using nirro blue tetrazolium and 5-bromo-4-chloro-3-indolyl phosphate as chromogens (Sigma). The immunoreaction on the Western blot was specifically blocked after preincubation of the antibodies with the corresponding peptide immunogens. Cross-reactivity with the second goat anti-rabbit antibody was excluded by appropriate controls (Cetin et al. (1994) Proc Natl Acad Sci USA 91, 2935-2939; Kulaksiz et al. (2002) Proc Natl Acad Sci USA 99, 6796-6801; Kulaksiz et al. (2002) Am J Pathol 161, 655-664; Cetin et al. (1995) Proc Natl Acad Sci USA 92, 5925-5929)

Immunohistochemistry and Immunofluorescence

Tissues were fixed in 4% paraformaldehyde for 18 h at 4° C. After dehydration in graded ethanol series, the specimens were embedded in paraffin. Paraffin sections (5 µm) were immunostained for hepcidin (antibodies EG(1)-HepN, EG(2)-HepN, and EG(1)-HepC, each diluted 1:2000) or TfR2 (antibody BT-TFR21-S. diluted 1:1000) by the avidin-biotin-peroxidase complex (ABC) technique and incubation sequences as previously described (Kulaksiz et al., (2002) Proc. Natl. Acad. Sci. USA 99, 6796-6801; Iculaksiz et al., (2002) Am. J. Pathol. 161, 655-664). The sections were incubated with the respective antibodies for 24 h at 4° C., followed by incubation with biotinylated anti-rabbit IgG (Jackson Immunoresearch, West Grove, Pa., USA) for 30 min diluted 1:200. The sections were then incubated for 30 min with a preformed complex of biotin-peroxidase/streptavidin (Jackson Immunoresearch), diluted in PBS (final concentrations: biotin-peroxidase, 0.7 µg/ml; streptavidin, 5 µg/ml). The antigen-antibody binding sites were visualized by incubation of the sections in 07 mM diaminobenzidine hydrochloride/ 0.002% H202 in 0.05 M Tris-HCl pH 7.6).

For immunofluorescence microscopy, tissue sections from human liver (2-4 µm) were prepared with a cryotome (FrigoCut 2800E; Leica, Nussloch, Germany), air dried for 2 hours, and fixed for 10 min in cold acetone (−20° C.). Double-immunofluorescence labeling was performed as described previously (Rost et al., (1999) Hepatology 29, 814-821) using the specific hepcidin antibodies (diluted 1:1000) and monoclonal antibody C219 (Id.) raised against canalicular P-glycoproteins (Centocor, Malvern, Pa.) diluted 1:30. After incubation with the respective antisera, staining was performed by incubation with Cy2-(1:200) and Cy3-(1:600) labeled antibodies against mouse and rabbit IgG (Dianova, Hamburg, Germany). Micrographs were taken with an Olympus AX70 microscope equipped with a digital camera (color view 12, soft imaging system SIS, Munster, Germany) and analysis software (SIS, Münster, Germany).

Specificity Controls

Method-dependent non-specificities were excluded by running controls as described (Cetin et al., (1994), Proc. Natl. Acad. Sci. USA 91, 2935-2939; Cetin et al., (1995) Proc. Natl. Acad. Sci. USA 92, 5925-5929). Antibody specificities were tested by preadsorption of the antibodies with homologous and heterologous antigenic peptides (6.25 100 µg/ml of the antiserum) (Kulaksiz et al., (2002) Proc. Natl. Acad. Sci. USA 99, 6796-6801; Kulaksiz et al., (2002) Am. J. Pathol. 161, 655-664). Preadsorption of the antibodies with homologous antigens at concentrations as low as 6.25 µ/ml completely blocked immunostaining in the liver tissues and cells, while preadsorption of the antibodies with heterologous antigens at concentrations up to 100 µg/ml had no effect on immunostaining.

Hepcidin ELISA Competitive Binding Assay

Serum samples were obtained from 26 healthy individuals (13 women, 13 men, aged 26-64, mean 43 yrs), from 35 patients with HH homozygous for the C282Y mutation in HFE (14 women, 21 men, aged 23-82 years, mean 54 years), with (15 patients) and without (20 patients) bloodletting therapy, and from 59 patients with renal insufficiency undergoing chronic hemodialysis (33 women, 26 men, aged 26-96 years, mean 57 years). During sample collection it was taken care that the patients had no infection. 19 patients of the group of renal insufficiency had renal anemia characterized by hemoglobin of maximum 11 g/dl. All patients with chronic renal insufficiency were treated 2-3 times a week with 3,000 IE recombinant human erythropoietin (EPO). 10 ml blood samples were withdrawn into ice-chilled serum-tubes and centrifuged at 2,500×g for 10 min at 4° C. Determinations were performed in duplicate using 96-well-microtiter plates coated with 200 µl/well rabbit antihepcidin antibody EG(2)-HepN diluted 1:4000 in Tris buffered saline (TBS) containing 40 mM Tris-HCl (pH 7.3), 100 mM NaCl. 50 µl standards containing various amounts of synthetic peptides (0, 20, 100, 500, and 1000 ng/ml) or human serum samples and 150 µl N-terminally biotinylated hepcidin-(28-47) (Peptide Specialty Laboratories GmbH, Heidelberg, Germany) (2 ng/well) were added to each well and incubated for 1 hour at RT. After washing with TBST (TBS with 0.05% Tween 20), the biotinylated antigen-antibody complexes were detected by streptavidin-peroxidase enzyme (Dako, Hamburg, Germany) with the substrate tetramethylbenzidine (DRG Instruments GmbH, Marburg, Germany); the color reaction was stoped with 1 M $H_2SO_4$ and the extinction of the solution was read at 450/630 nm wavelength.

Measured values of hepcidin in the four groups of interest were entered in an EXCEL spreadsheet and evaluated using SAS WIN Version 8.2. The measured values were summarized by means of the following summary statistics by diagnosis group: the number of observations, the arithmetic mean, standard deviation, minimum, median and maximum. Possible differences between groups were analyzed with pairwise Wilcoxon U-tests. The level of significance was set to 5% (0.05). The correlation between prohepcidin and iron, ferritin or transferrin was analyzed by the Spearman rank correlation.

Expression of Hepcidin and TfR2 in the Liver and HepG2 Cells

RT-PCR analysis demonstrated that hepcidin is expressed in human liver (Gehrke et al. (2003) Blood MS#2002-11-3610.R2). Similarly, a 192-bp expected PCR product was detected in HepG2 cells (control), which were already shown to express hepcidin (Pigeon C et al. (2001) J Biol Chem 276, 7811-7819; Gehrke et al. 47 (2003 (FIG. 2, A). In addition, RT-PCR analyses clearly revealed that TfR2 is expressed in the human liver and HepG2 cells (data not shown).

In Western blot analysis, all hepcidin antibodies [EG(1)-HepN, EG(2)-HepN, and EG(1)-HepC] coincidentally identified an immunoreactive band of ~10 kDa in extracts of human and guinea pig liver. This liver peptide comigrated with an immunoreactive band recognized by the hepcidin antibodies in homogenates of HepG2 cells (FIG. 2, B-ID). All antibodies also identified an immunoreactive protein-at ~20 kDa in all lanes loaded with human and guinea pig liver extracts or HepG2 cell extracts. Western blot analysis of skeletal muscle extracts (control) showed neither the immunoreactive band of 10 kDa nor the band at 20 kDa (FIG. 2, B-D). Western blot analysis with TfR2 antibody BT-TFR21-S resulted in a staining of an expected (Fleming et al., (2000) Proc. Natl. Acad. Sci. USA 97, 2214-2219)-105 kDa protein in extracts of mouse liver. In extracts of human liver and HepG 2 cells, a ~95 kDa immunoreactive TfR2 and to lesser extent a ~105 kda immunoreactive protein was recognized by the same antibody (data not shown). No immunoreactivity was detected in the heart (control tissue).

Immunofluorescence in HepG2 Cells

Figure 3A:
FIG. 3 illustrates detection of hepcidin in HepG2 cells by immunofluorescence microscopy using the antibodies EG(1)-HepN (A), EG(2)-HepN (B), and EG(1)-HepC (C) (Scale bar 8 µm)
Figure 3B:
Figure 3C:
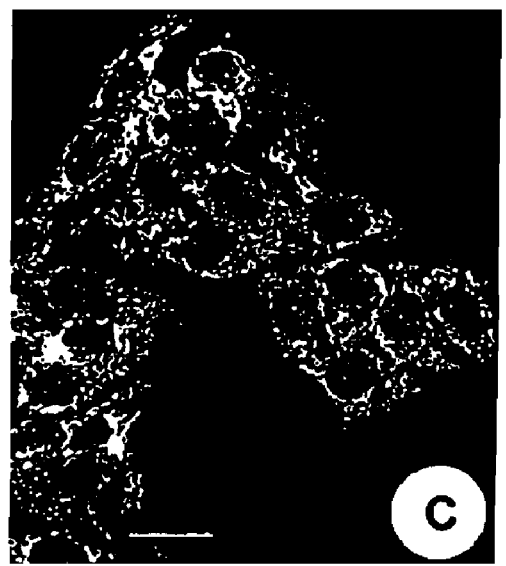
Figure 4A:
FIG. 4 illustrates the cellular localization of hepcidin in guinea pig (A-F) and human (G-I) liver. The paraffin sections immunostained with the region-specific antibodies EG(1)-HepN (A, D, 25 G), EG(2)-HepN (B, E, H) and EG(1)-HepC (C, F, I) show a distinct immunoreactivity at the basolateral membrane domain of hepatocytes (arrows). (Magnification: A-C, ×180; D-I, ×540).
Figure 4B:
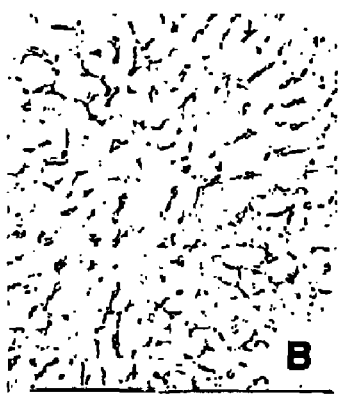
Figure 4C:
Figure 4D:
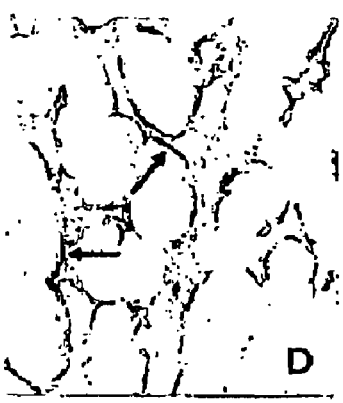
Figure 4E:
Figure 4F:
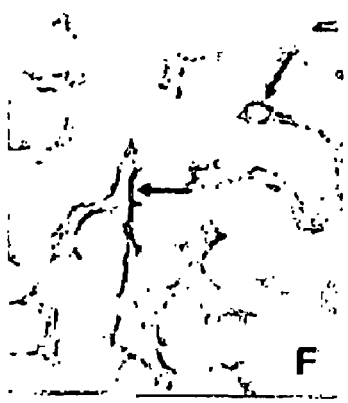
Figure 4G:
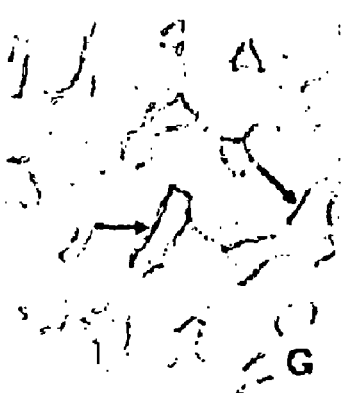
Figure 4H:
Figure 4I:
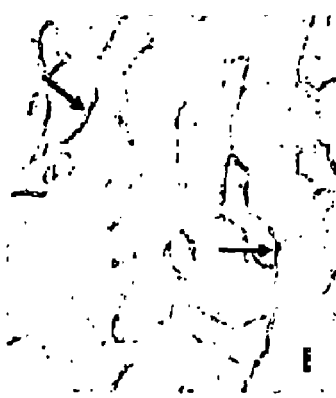

Using epitope specific anti-hepcidin antibodies, expression of hepcidin peptide in HepG2 cells was investigated by immunofluorescence analysis. All antibodies similarly identified hepcidin in HepG2 cells resulting in a strong immunoreactivity (FIG. 3). Coincident with the cellular localization of hepcidin, the TfR2 antibody detected TfR2 in the same cells (data not shown)

Cellular and Subcellular Localization of Hepcidin and TfR2.

Figure 5A:
FIG. 5 illustrates immunohistochemical sections of guinea pig liver (A, antibody EG(1)-HepN; B, antibody EG(2)-HepN: C, antibody EG(1)-HepC showing the clear zonation of hepcidin within the hepatic lobules with decreasing immunoreactivity from periportal zones (stars) towards the central veins (arrowheads). Note that no immunoreactivity is found in hepatocytes around the central veins. (The arrow in B indicates a portal triad.) (A-C, ×180).
Figure 5B:
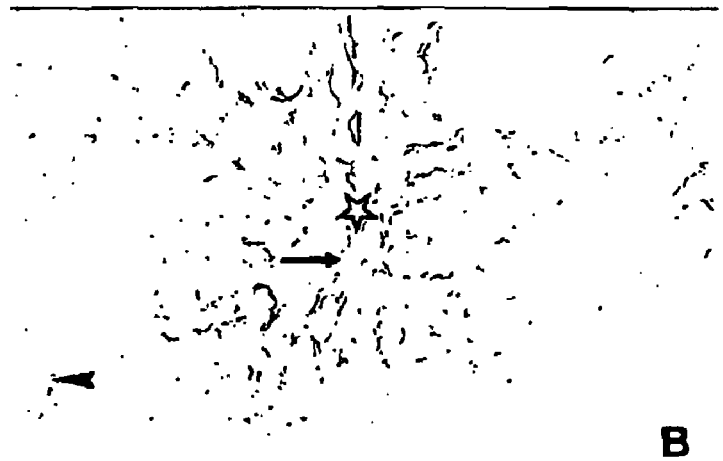
Figure 5C:

Immunohistochemical studies with various region-specific antibodies consistently localized hepcidin to the hepatocytes in human liver (FIG. 4). The Kupffer cells, endothelial cells, bile ducts, and the vascular system completely lacked hepcidin immunoreactivity. The same antibodies detected a strong hepcidinimmunoreactivity also in guinea pig liver (FIG. 4). Hepatic lobules were heterogeneous with respect to the hepcidin immunoreactivity: within a hepatic lobule, the hepcidin immunoreactive cells were predominantly located in periportal zones, and the frequency of hepcidin-positive cells continuously decreased from the portal triads toward the central veins (FIG. 5). Notably, distinct intercellular differences existed between the hepcidin positive cells: while most hepatocytes were strongly positive for hepcidin, others displayed only a faint staining or were totally unreactive for hepcidin (FIG. 5). At the subcellular level, hepcidin immunoreactivity was confined to the basolateral (=sinusoidal) membrane domain of hepatocytes by immunohistochemistry; no immunoreactivity was found at the apical membrane domain of the respective cells (FIG. 2). Similarly, immunofluorescence analysis demonstrated a strong immunoreactivity for hepcidin at the basolateral membrane domain; immunoreactivity was absent from the apical membrane domain as revealed by double staining with the C219 antibody raised against canalicular P-glycoproteins (Rost et al. (1999) Hepatology 29, 814-821) (data not shown).

Corresponding to the localization of hepcidin, protein-specific antibody BT-TFR21-S detected TfR2 in human and mouse liver. At the cellular level, TfR2 was found at the basolateral membrane of hepatocytes, which revealed distinct intercellular differences concerning the intensity of immunoreactivity (data not shown). Heterogeneity was also observed within a hepatic lobule with increasing immunoreactivity from the central veins to the portal triads.

Detection of Hepcidin Propeptide in Human Plasma

Figure 6:
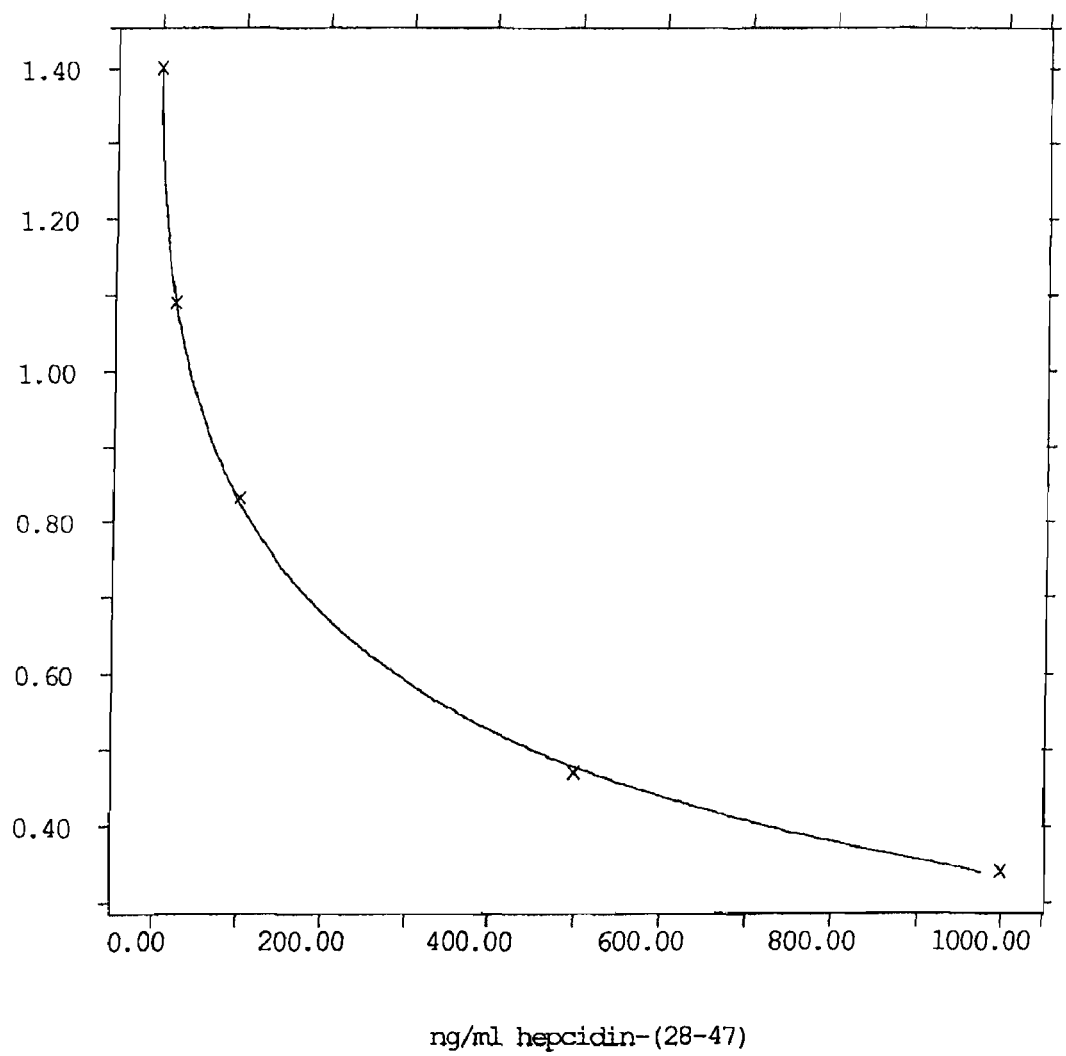
FIG. 6 illustrates ELISA results for circulating human prohepcidin. A representative standard curve with concentrations of hepcidin-(28-47) (SEQ ID NO: 3) in ng/ml and the extinction of the ELISA solution at 450 nm wavelength are shown. Note the high resolving power in the range of 4 to 400 ng/ml hepcidin-(28-47).

A stable pro-hepcidin ELISA assay (DRG Instruments GmbH, Marburg, Germany) with high reproducibility and sensitivity was developed with the specific N-terminal hepcidin antibody EG(2)-HepN. As seen in FIG. 6, the ELISA revealed the highest resolving power between 4 and 400 ng/ml, a range, where pro-hepcidin concentrations in human serum were determined. As specificity control, the incubation in ELISA was performed with heterologous peptides. No crossreactivity was observed when heterologous peptides were used. The presence of pro-hepcidin in blood was verified by Western blotting analysis. All hepcidin antibodies identified in extracts of human serum a single hepcidin immunoreactive band of ~10 kDa molecular mass that comigrated exactly with the immunoreactive hepcidin in liver tissues and HepG2 cell extracts (FIG. 2, B-D)

ELISA Characteristics

The sensitivity of the assay was 3.95 ng/ml. There was no overlap with the lowest standard (20 ng/ml). Serial dilutions of human pro-hepcidin, dissolved in the zero standard, run parallel to the standard curve of the pro-hepcidin ELISA with the range of recovery between 90.6-111.6%. Recovery expressed as percentage of observed from expected concentration was between 91.8 and 105.7%. Good precision was demonstrated (total CV<10%) at three concentrations of pro-hepcidin tested across the assay range.

Pro-Hepcidin Levels in Hereditary Hemochromatosis, Chronic Renal Insufficiency, and Renal Anemia Using the sensitive hepcidin ELISA, pro-hepcidin in the range from 51.6-153.4 ng/ml serum (mean±SE; 106.2±32.1 ng/ml) was detected in the healthy control group of 26 volunteers (table 1). In patients with HH, the concentrations of pro-hepcidin were 12.1 to 153.9 ng/ml serum (mean±SE; 70.2±38.1 ng/ml). These concentrations were significantly lower compared to that in control subjects (P<0.05) (table 1). The pro-hepcidin concentrations varied from 31.1 to 471.3 ng/ml (mean±SE; 1481±88.0 ng/ml) in serum of patients suffering from CRI and were significantly increased compared with that in control subjects (P<0.01) and HH(P<0.001). In contrast, pro-hepcidin levels in hemodialysis patients with RA were significantly decreased (115.0±53.1 ng/ml; range, 20.5-252.4 ng/ml) (P=0.05) compared to patients with CRI (table 1)

No significant correlation was found in our samples (serum from HH, CRI, and RA) between pro-hepcidin and iron, ferritin or transferrin saturation. The test of difference from zero showed no significance.

TABLE 1

RESULTS OF PAIRWISE U-TESTS (P-VALUE)

| | Chronic Renal Insufficiency | Renal Anemia | Hemochromatosis |
|---|---|---|---|
| Control | 0.0419 | 0.6131 | <0.0005 |
| Chronic Renal Insufficiency | | 0.23 | <0001 |
| Renal Anemia | | | 0.002 |

Discussion

RT-PCR analyses with specific primers showed that hepcidin is highly expressed in HepG2 cells (control), a well-differentiated hepatocellular carcinoma cell line (Aden et al. (1979) Nature 282, 615-616) demonstrating in many aspects the physiology of normal hepatocytes. Using the appropriate primer specifications and combinations successfully employed in HepG2 cells, the RT-PCR studies confirmed expression of hepcidin in the human liver. Three different antibodies recognizing different epitopes in the hepcidin precursor molecule (FIG. 1) concurrently identified an immunoreactive peptide of ~10 kDa by Western blot analysis not only in HepG2 cells but also in liver extracts of two species, man and guinea pig. The apparent molecular mass of this immunoreactive peptide is in accordance with the predicted molecular mass deduced for the hepcidin prohormone from the cDNA sequence (Pigeon C et al. (2001) J Biol Chem 276, 7811-7819) (FIG. 1). Interestingly, a second immunoreactive band of ~20 kDa was detected by all hepcidin antibodies in extracts of HepG2 cells and human and guinea pig liver but was lacking in the control tissue. This immunoreactive protein may reflect a dimeric type of hepcidin. In fact, in a previous study an aggregation property and a possible formation of multimers were described for hepcidin-25 but not for hepcidin-20 (Hunter et al. (2002) J Biol Chem 277, 37597-37603).

Immunocytochemical studies with the region- and molecular domain-specific hepcidin antibodies revealed a strong immunoreactivity in HepG2 cells demonstrating expression of hepcidin in these cells as already shown by molecular biological techniques (Gehrke et al. (2003) Blood MS#2002-11-3610.R2). Immunohistochemical and immunofluorescence investigations with these different hepcidin antibodies indicated that, in human and guinea pig liver, hepcidin is specifically localized in hepatocytes mainly located around the portal triads. The coincident staining by different region-specific antibodies not only in the human and guinea pig liver but also in the HepG2 cells points to hepatocytes being the source of hepcidin. Hepcidin immunoreactivity decreased from the periportal zones towards the central veins. This zonation within the portal lobules may have a functional significance, since the periportal hepatocytes have first-pass access to portal veins bringing iron-rich blood from the gut. Notably, distinct intercellular differences existed between the hepcidin-positive cells with respect to the density of hepcidin immunoreactivity that may reflect intercellular differences in expression or secretion of hepcidin.

At the subcellular level, hepcidin was concentrated at the basolateral membrane domain of hepatocytes. No immunoreactivity was found at the apical membrane domain. The discrete distribution pattern of hepcidin at the subcellular level may infer a basolaterally directed release of hepcidin into the liver sinusoids. This directional secretion route is additionally substantiated by the detection of hepcidin prohormone (FIG. 1) in human serum (see below); consequently, these findings provide further evidence that hepatocytes may regulate iron metabolism in an endocrine fashion via the secretion of prohepcidin.

To analyze the expression and cellular distribution of TfR2 as well as the respective target membrane domains, RT-PCR, Western blot and immunohistochemical studies at the cellular level were performed. As shown in previous studies RT-PCR analyses revealed that TfR2 is highly expressed in human liver. (Fleming et al., (2000) Proc. Natl. Acadi. Sci. USA 97, 2214-2219). The presence of this protein was confirmed by Western blot studies using BT-TFR21-S antibody specific to human and mouse TfR2. A ~105 kDa immunoreactive protein was detected in mouse liver extracts; this molecular mass of immunoreactive TfR2 is slightly larger than the expected 95 kDa (Fleming et al., (2000) Proc. Natl. Acadi. Sci. USA 97, 2214-2219) and may represent some posttranslational modifications as described previously (Kawabata et al., (2000) J. Biol. Chem. 275, 16618-16625). Under identical conditions, however, the TfR2-antibody identified the protein at the expected 95 kDa molecular mass and with a lower affinity the 105 kDa protein in human liver extracts. The discrepancy between the immunoblots of human and mouse liver may be due to interspecies differences.

Immunohistochemical investigations revealed that TfR is localized to hepatocytes of human and mouse liver; coincident with the cellular distribution of hepcidin, the protein-specific antibody localized TfR2 exclusively at the basolateral membrane. This type of membrane-specific association of TfR2 argues particularly for a basolateral activation of TfR2, which is involved in iron metabolism by binding diferric transferrin and mediating uptake of transferrin-bound iron from the blood into hepatocytes (Philpott, C. C. (2002) Hepatology 35, 993-1001; Subramaniam et al., (2002) Cell Biochem. Biophys. 36, 235-239). Notably, a similar lobular zonation as described for hepcidin was observed for TfR2 with decreasing immunoreactivity from the periportal zones toward the central veins.

Since an interaction between hepcidin and TfR2 at the cellular level has been discussed in previous studies (Nicolas et al., (2001) Proc. Natl. Acad. Sd. USA 98, 8780-8785; Frazer et al., (2002) Gastroenterology 123, 835-844), the coexistence of hepcidin and TfR2 in HepG2 cells a well-differentiated hepatocellular carcinoma cell line (Aden et al., (1979) Nature 282, 615-616) was analyzed, demonstrating in many aspects the physiology of normal hepatocytes. RT-PCR studies using the appropriate primer specifications and combinations successfully employed in the human liver identified expression of hepcidin and TfR2 in HepG2 cells. At the translational level, the presence of hepcidin and TfR2 in HepG2 cells was confirmed by Western blot studies that yielded immunoreactive protein bands of correct molecular weights, comigrating with the corresponding immunoreactive bands from the liver tissues. The co-localization of the respective proteins in HepG2 cells was particularly substantiated by immunocytochemistry using the corresponding region- and molecular domain-specific antibodies. All antibodies demonstrated hepcidin-labeling in HepG2 cells, revealing a granular immunoreactivity pattern in these cells that infers localization of the peptide to small secretory vesicles, already demonstrated in hepatocytes by electron microscopy (Schwartz et al., (1985) EMBO J. 4, 899-904). TfR2 was immunocytochemically localized, with a peculiar distribution pattern, to HepG2 cells.

On the basis of present data at the transcriptional and translational level, hepcidin and TfR2 are coexpressed in the liver and colocalized at the basolateral membrane domain of hepatocytes. In addition to a coincident localization of TfR2 and hepcidin at the cellular level, a similar distribution of these molecules within the hepatic lobules with a concentrated immunoreactivity in periportal zones and a decreasing straining toward the central veins was also detected. The coordinate expression of these proteins in a common (basolateral) membrane domain and their similar lobular zonation argue for a morphofunctional coupling of the regulating peptide hormonohepcidin and the transferrin-bound iron uptake via TfR2. Indeed, different data substantiate the interaction between hepcidin and TfK2. First, alterations in transferrin saturation, probably sensed by TfR2, modulate the expression of hepatic hepcidin (Philpott, C. C. (2002) Hepatology 35, 993-1001). Second, as revealed from quantitative RT-PCR analyses on human liver, hepatic expression of TfR2 correlates significantly with hepcidin expression regulated by the transferrin saturation (S. G. Gehrke, H. Kulaksiz et al. unpublished data). Third, hepcidin and TfR2 are colocalized at a common cell membrane domain and reveal the same lobular distribution with a strong immunoreactivity in periportal zones, the site, where in case of mutations that abrogate expression of TfR2 (Fleming et al., (2002) Proc. Natl. Acad. Sci. USA 99, 10653-10658) and hepcidin (Nicolas et al., (2001) Proc. Natl. Acad. Sci. USA 98, 8780-8785) but also hepcidin (Zhou et al., (1998) Proc. Natl. Acad. Sd. USA 95, 2492-2497; Levy et al., (1999) Blood 94, 9-11) and B2m (Santos et al., (1996) J. EZp. Med. 184, 1975-1985) hepatic iron overloading occurs. Fourth, mutations in the TfR2 gene were reported to lead to hemoechromatosis (Camasehella et al., (2000) Nat. Genet. 25, 14-15); this may result from decreased hepcidin expression, which, in turn, results in increased iron absorption (Nicolas et al., (2001) Proc. Natl. Acad. Sd. USA 98, 8780-8785).

The simultaneous existence of hepcidin and TfR2 in HepG2 cells and their common polarized localization and lobular distribution in the liver may indicate that hepcidin is an intrinsic hepatic peptide morphofunctionally coupled to TfR2, which is regulated by transferrin saturation and, in turn, modulates expression of hepcidin. Hence, pertinent findings are expected from studies on the signaling pathway of hepcidin.

Since blood-forming tissues and sites of iron storage, such as the liver, transmit signals to the intestinal cells that indicate the body's requirements for dietary iron (Philpott C. C. (2002) Hepatology 35, 993-1001), hepcidin is a candidate signaling factor secreted from the hepatocytes and regulating the intestinal iron absorption. However, prior to the present invention, there was controversy about the existence of certain molecular forms of hepcidin in the blood (Krause et al. (2000) FEBS Lett 489, 147-150; Park et al. (2001) J Biol Chem 276, 7806-7810; Hunter et al. (2002) J Biol Chem 277, 37597-37603).

To analyze whether the prohormone of hepcidin is secreted into the blood, and to assess the range of prohepcidin levels in human serum of healthy volunteers and of patients with different diseases, an ELISA was developed by applying the N-terminal antibody EG(2)-HepN raised against hepcidin prohormone. Although the C-terminal antibody EG(1)-HepC revealed specific results in dot blot (data not shown), Western blot, immunohistochemistry, and immunofluorescence experiments (FIGS. 1-4), no immunoreactivity could be obtained in ELISA. The compact folding pattern of hepcidin and its tertiary structure in the blood may account for the inability of the EG(1)-HepC antibody to identify circulating hepcidin.

The ELISA with antibody EG(2)-HepN was characterized by a high reproducibility, stability and sensitivity with a detection limit of 3.95 ng/well and a powerful resolution in the range of 4 to 400 ng/ml; the range, where hepcidin concentrations were determined. In human serum from healthy individuals (n=26), prohepcidin was measured in the range from 51.6 to 153.4 ng/ml (mean±SE; 106.2±32.1 ng/m].), which is comparable with the concentration of known regulating peptide hormones and approximately 11-fold higher than the concentration of hepcidin in human urine (Park et al. (2001) J Biol Chem 276, 7806-7810). Interestingly, the measured concentrations exhibited a wide range of prohepcidin indicating that the peptide may be subject to strong regulation.

The cDNA structure suggests that hepcidin is translated as an 84 aa prepropeptide that is N-terminally processed to the 20-25 amino acid peptides (Park et al. (2001) (FIGS. 1 and 7). Although a strong consensus sequence for a signal sequence cleavage site is located between $Gly^{24}$ and $Ser^{25}$ that would result in a 60 residue propeptide, previous studies failed to isolate the larger propeptide from native sources like liver tissue and blood (Park et al. (2001)). In addition to technical difficulties, the abundance of propeptide convertases in the liver may inhibit the isolation of certain propeptides. In this context, recent studies have shown that the human circulating form of hepcidin, described by two research groups in blood (Krause et al. (2000) FEBS Lett 489, 147-150) and in urine (Park et al. (2001) J Biol Chem 276, 7806-7810), consists of the C-terminal 20-25 amino acids of the protein. However, ELISA measurements of the present invention were performed with the specific-antibody raised against the N-terminus of hepcidin precurcor, implying that besides the 20-25 amino acid processed forms the hepcidin prohormone is secreted and circulates in human blood. Indeed, the potential release of prohepcidin into the blood was confirmed by Western blot analysis. All hepcidin antibodies identified in extracts of human serum a single hepcidin band of ~10 kDa that comigrated exactly with the immunoreactive hepcidin in tissue extracts of the liver and HepG2 cells (positive control; FIG. 1). Hepcidin fragments smaller than 10 kDa were not detected. The presence of prohepcidin in the human serum indicates that hepatocytes secrete the prohormone of hepcidin that may decrease dietary iron absorption via an endocrine pathway.

To analyze the significance of hepcidin in patients with iron overload, the present invention provides hepcidin concentrations in serum of 35 HH patients homozygous for C282Y mutation in HFE with the typical characteristics of iron overload detected in all HH patients under study. Hepcidin concentrations were not increased in these individuals to reduce the intestinal iron absorption as supposed previously (Fleming and Sly (2001) Proc Natl Acad Sci USA 98, 8160-8162). Prohepcidin levels in serum of HH patients were unexpectedly downregulated, not only in untreated patients, but also in individuals undergoing a weekly bloodletting therapy. Compared to healthy volunteers, the prohepcidin concentrations were markedly reduced from 106.2 to 70.2 ng/ml serum. No difference was observed between treated and untreated HH patients. These findings are in line with previous HH studies showing that the liver hepcidin expression is significantly decreased in the hfe knockout mouse (Ahmad et al. (2002) Blood Cells Mol Dis 29, 361-366; Muckenthaler et al. (2003) Nat Genet 34, 102-107) and in patients with HFE-associated hemochromatosis. They are also in accordance with in vitro studies demonstrating that iron loading of primary human hepatocytes and HepG2 cells downregulate hepcidin mRNA (Gehrke et al. (2003) Blood MS#2002-11-3610.R2; Nemeth et al. (2003) Blood 101, 2461-2463). Since iron absorption is enhanced in HH despite iron overload (Pietrangelo A. (2002) Am J Physiol Gastrointest Liver Physiol 282, G403-414; Philpott C. C. (2002) Hepatology 35, 993-1001; Anderson and Powell (2002) Int J Hematol 76, 203-207), and constitutive hepcidin expression prevented iron overload in a mouse model of hemochromatosis (Nicolas et al. (2003) Nat Genet 34, 97-101), it is assumed that the hepcidin regulation is disrupted in HH patients. The depressed concentrations of hepcidin are obviously not able to inhibit sufficiently the elevated intestinal iron absorption. Moreover, based on the findings that the liver hepcidin expression is significantly decreased in the hfe knockout mouse (Ahmad et al. (2002) Blood Cells Mol Dis 29, 361-366; Muckenthaler et al. (2003) Nat Genet 34, 102-107) and in HH patients (Bridle et al. (2003) Lancet 361, 669-673), the lack of prohepcidin upregulation in HH despite iron overload indicates that HFE may be involved in the regulation of serum hepcidin levels.

Although previous studies have demonstrated that urinary hepcidin excretion correlates well with serum ferritin concentrations (Nemeth et al. (2003) Blood 101, 2461-2463), in the present study, no correlation was found between the circulating prohepcidin and the serum iron or ferritin levels in HH or dialysis patients. Likewise, no correlation was detected between prohepcidin and the transferrin saturation, which is supposed to regulate the expression of liver hepcidin (Gehrke et al. (2003)), although the HH patients under study were not affected by anemia, hypoxia or inflammation, representing hepcidin influencing parameters. The data suggests that the regulation of prohepcidin levels in the serum by iron stores involves complex indirect effects (Nemeth et al. (2003) Blood 101, 2461-2463).

Since hepcidin has also been isolated from urine, the present invention provides for the evaluation of hepcidin regulation in renal insufficient patients. In contrast to HH patients and to healthy subjects, concentrations of immunoreactive prohepcidin in the serum of patients with CRI were significantly increased from 106.2 ng/ml in healthy subjects to 148.1 ng/ml. Enhanced levels of prohepcidin in dialysis patients suggests that the kidneys may be involved in the metabolism and/or elimination of the circulating peptide. However, it is presently unclear if the urinary hepcidin is only filtered from the blood or originates from the kidney. Based on the present invention, it cannot be excluded that hepcidin is released at least partly from the kidneys, since it was also found in renal tubular cells (Kulaksiz et al. (2003) unpublished data).

The present invention provides for a determination of prohepcidin serum levels in dialysis patients with RA, a well recognized complication of progressive renal failure, which is characterized by normochromic, normocytic erythrocytes. In comparison to healthy subjects, the immunoreactive prohepcidin concentrations were not significantly higher in patients with RA (mean, 115.0 ng/ml). Despite the terminal renal insufficiency in these patients leading to accumulation of the peptide hormone, the prohepcidin levels were significantly lower than in dialysis patients without anemia (mean, 148.1 ng/ml). From the present invention it is concluded that hepcidin regulation in RA is different than that in anemia of inflammation or of hepatic adenomas. Downregulation of prohepcidin in RA reflects a reactive physiological modulation of the peptide to enhance intestinal iron absorption and iron release from reticuloendothelial macrophages. The present invention provides that prohepcidin is increased in the group of patients with CRI without anemia despite EPO therapy. Thus, it is concluded that hepcidin is decreased in RA because of blood loss, which may be a reason for hepcidin downregulation (Nicolas et al. (2002) J Clin Invest 110, 1037-1044).

The present invention provides an ELISA to measure prohepcidin levels in human serum. This assay is non-invasive and easy to perform, thus appropriate for routine work. The prohepcidin assay is due to its precision, sensitivity, reproducibility and exact determination of hepcidin-(28-47) of human serum samples. Application of the present ELISA allows for the first time the detection and determination of prohepcidin in patients suffering from several disorders of iron metabolism. Further studies are required to identify the exact molecular mechanism of prohepcidin action in various iron states. The present invention also provides that hepcidin agonists and antagonists should be potential drugs in the prevention and treatment of iron disorders.

To understand the role of hepcidin, knowledge about the cellular origin and the signaling pathway of the peptide is necessary. In this respect, the present invention describes hepcidin immunoreactivity in human and guinea pig liver, where it is localized to the basolateral membrane domain of hepatocytes. Previous studies have speculated on a possible connection between these cells and the absorptive enterocytes (Hunter et al., (2002) J. Biol. Chem., M205305200; Anderson et al., (2002) Biochem. Soc. Trans. 30, 724-726). The present invention describes the detection of prohepcidin in the human plasma thereby indicating that hepatocytes secrete the prohormone of hepcidin that may decrease dietary iron absorption via an endocrine pathway. Moreover, hepcidin was detected in HepG2 cells, where the newly discovered transferrin receptor type 2 was also found (data not shown).

Enzyme Immunoassay for the Quantitative Measurement of Hepcidin in Human or Animal Serum and Other Body Fluids.

In one embodiment of the invention a Hepcidin enzyme immunoassay ("EIA") is used. An EIA is a solid phase enzyme-linked immunosorbent assay (ELISA) based on the competitive principle. Microtiter wells of a 96 well microtiter plate are coated with a polyclonal rabbit anti-hepcidin antibody directed against Hepcidin-(28-47). An unknown amount of Prohepcidin present in the sample and a fixed amount of Hepcidin-(28-47) conjugated with a biotin molecule compete for the binding sites of the Hepcidin antibodies immobilized on the wells. After one hour incubation the microtiter plate is washed to stop the competition reaction. In the following incubation the bound biotin molecules are detected with streptavidin horseradish peroxidase. After one half hour of incubation the plate is washed a second time. Having added the substrate solution the concentration of Hepcidin is inversely proportional to the optical density measured.

Materials:

Microtiter wells; wells coated with Anti-Hepcidin antibody (96 wells); Reagent: Biotin Conjugate (Hepcidin conjugated to biotin) 7 ml.; Reference Standard Set, 1.0 ml each; 0, 20, 100, 500, 1000, 2000 ng/ml; Prohepcidin Controls, low and high, 2 vials (lyophylizate); Reagent: Enzyme Complex (Streptavidin conjugated to horseradish peroxidase ("HRP")) 14 ml; Reagent: Substrate Solution-HS-TMB, 14 ml; Stop Solution, 0.5M $H_2SO_4$, 14 ml; Wash Solution, 40×, 30 ml; A microtiterplate reader (450±10 nm) (e.g., the DRG Instruments Microtiterplate Reader); Precision micropipettes with disposable tips for 50 and 100 µl; Standard refrigerator; Absorbent paper; Deionized water.

While this embodiment has been described in terms of preferred materials, a person skilled in the art of the invention will appreciate that other materials can be used in the invention. For example, one of skill in the art will appreciate that complementary binding moieties other than biotin/streptavidin, as well as enzyme/substrate combinations other than horse radish peroxidase/peroxide, may be used in the invention.

Storage Conditions.

When stored at 2° to 8° C. unbroken reagents will retain reactivity until expiration date. Do not use reagents beyond this date. Microtiter wells must be stored at 2° to 8° C. Once the foilbag has been broken care should be taken to close it tightly again. The immuno-reactivity of the coated microtiter wells is stable for approx. 6 weeks in the broken, but tightly closed plastic zip pouch containing the desiccant.

Specimen Collection and Preparation.

Human or animal serum or EDTA plasma should be used in the assay. No special pretreatment of the biological sample is necessary. The biological sample may be stored at 2-8° C. for up to 24 hours, and should be frozen at −20° C. or lower for longer periods. Do not use grossly hemolyzed or grossly lipemic specimens. For other sample material a special extraction protocol may be necessary.

Performance of the Assay: General Remarks:

All reagents and specimens must be allowed to come to room temperature before use. All reagents must be mixed without foaming.

Once the test has been started, all steps should be completed without interruption.

Use new disposable plastic pipette tips for each reagent, standard or specimen in order to avoid cross contamination. For the dispensing of the Substrate Solution and the Stop Solution avoid pipettes with metal parts.

Pipette standards and samples onto the bottom of the well. For pipetting of Enzyme Conjugate and Stop Solution it is recommended to hold the pipette in a vertical position above the well and dispense the correspondent solution into the center of the well so that a complete mixing of Enzyme Conjugate with sample or standard and of the Stop Solution with the Substrate Solution is achieved.

Before starting the assay, it is recommended that all reagents be ready, caps removed, all needed wells secured in holder, etc. This will ensure equal elapsed time for each pipetting step without interruption.

As a general rule the enzymatic reaction is linearly proportional to time and temperature. This makes interpolation possible for fixed physico-chemical conditions. If in a test run the absorbance of Zero Standard is lower than 1.0 or above the upper performance limit of your microtiterplate spectrophotometer you can extend or reduce the incubation time of the final enzymatic formation of color to 30 or 10 minutes accordingly. Since calibrators are assayed in each run, absorbance fluctuations do not affect the result.

The Substrate Solution should be colorless or slightly blue or green. If the solution is dark blue the reagent is unusable and must be discarded.

During incubation with Substrate Solution avoid direct sunlight on the microtiter plate.

Reagent Preparation.

Reference Standards and Controls: Reconstitute the lyophilized contents of the standard/control vials with 1.0 ml bidistilled Water. Note: The reconstituted standards/controls are stable for 6 days at 2-8° C. For longer storage freeze at −20° C. Wash Solution: Add deionized water to the 40× concentrated Wash Solution (contents: 30 ml) to a final volume of 1200 ml. The diluted Wash Solution is stable for 2 weeks at room temperature.

Assay Procedure.

Secure the desired number of coated strips in the holder.
Dispense 50 µl of Hepcidin Standards into appropriate wells.
Dispense 50 µl of sample into selected wells.
Dispense 50 µl of Biotin Conjugate into each well.
Thoroughly mix the plate for 10 seconds. It is important to have complete mixing in this step.
Incubate for 60 minutes at room temperature.
Briskly shake out the contents of the wells.
Rinse the wells 3 times with diluted Wash Solution (400 µl per well). Strike the wells sharply on absorbent paper to remove residual droplets.
Add 100 µl Streptavidin HRP Complex to all wells.
Incubate for 30 minutes at room temperature.
Briskly shake out the contents of the wells.
Rinse the wells 3 times with diluted Wash Solution (400 µl per well). Strike the wells sharply on absorbent paper to remove residual droplets.
Add 100 µl of Substrate Solution to each well, at timed intervals.
Incubate for 15 minutes at room temperature.
Stop the enzymatic reaction by adding 100 µl of Stop Solution to each well at the same timed intervals as in step 10 and determine the absorbance of each well at 450±10 nm.

Final Reaction Stability.

It is recommended that the wells be read within 30 minutes following step 15.

Calculation of Results.

Any microwell reader capable of determining the absorbance at 450±10 nm may be used. The Testosterone value of each sample is obtained as follows:

a. Using linear-linear or semi log graph paper, construct an standard curve by plotting the average absorbance (Y) of each Reference Standard against its corresponding concentration (X) in ng/ml. For construction of the standard curve we recommend a four parameter logistic function.

b. Use the average absorbance of each sample to determine the corresponding Testosterone value by simple interpolation from this standard curve, multiplying by the initial sample dilution, if necessary.

A DRG ELIZA MAT 3000 and the DRG Regression Program allow the reading and computer assisted interpretation using a four parameter logistic function.

Example of a Standard Curve.

The following data is for demonstration only and cannot be used in place of data generations at the time of assay.

| Standard | OD at 450 nm |
|---|---|
| Standard 0 (0 ng/ml) | 1.79 |
| Standard 1 (20 ng/ml) | 1.67 |
| Standard 2 (100 ng/ml) | 1.33 |
| Standard 3 (500 ng/ml) | 0.82 |
| Standard 4 (1000 ng/ml) | 0.61 |
| Standard 5 (2000 ng/ml) | 0.43 |

Performance Characteristics Sensitivity.

FIG. 6. illustrates a representative ELISA for circulating human prohepcidin standard curve with concentrations of hepcidin(28-47) in ng/ml and the extinction of the ELISA solution at 450 nm wavelength.

TABLE 2

PROCEDURE FLOW SHEET DRG HEPCIDIN ELISA KIT

| Description | Standard/Sample µl | Biotin-Conjugate µl | | Streptavidin HRP Complex µl | | Substrate Solution µl | | Stop Solution µl | |
|---|---|---|---|---|---|---|---|---|---|
| Standard 0 | 50 | 50 | Mix for 10 seconds. Incubate for 60 minutes | 100 | Incubate for 30 minutes at room temperature. Rinse | 100 | Incubate for 15 minutes at room temperature | 100 | Read the OD at 450 nm with a Microtiterplate |

TABLE 2-continued

PROCEDURE FLOW SHEET DRG HEPCIDIN ELISA KIT

| Description | Standard/ Sample µl | Biotin- Conjugate µl | Streptavidin HRP Complex µl | | Substrate Solution µl | Stop Solution µl |
|---|---|---|---|---|---|---|
| Standard 1 | 50 | 50 | at room temperature | 100 | the wells 3 times | 100 | 100 | reader. |
| Standard 2 | 50 | 50 | Rinse the wells | 100 | with diluted | 100 | 100 |
| Standard 3 | 50 | 50 | 3 times | 100 | Wash | 100 | 100 |
| Standard 4 | 50 | 50 | with | 100 | Solution | 100 | 100 |
| Standard 5 | 50 | 50 | diluted | 100 | 400 | 100 | 100 |
| Standard 6 | 50 | | Wash Solution | 100 | µl/well | 100 | 100 |
| Sample 1 | 50 | 50 | 400 | 100 | | 100 | 100 |
| Sample 2 | 50 | 50 | µl/well. | 100 | | 100 | 100 |
| Sample 3 | 50 | 50 | | 100 | | 100 | 100 |
| Sample 4 | 50 | 50 | | 100 | | 100 | 100 |
| Sample 5 | 50 | 50 | | 100 | | 100 | 100 |

The analytical sensitivity was calculated from the mean minus 2 SD (SD=0.055) of 21 replicates (n=21) analysis of zero standard.

The sensitivity of the assay is 3.95 ng/ml. The linearity of the assay was evaluated by diluting of the samples (serum) having different Hepcidin levels with zero standard. The Hepcidin content in the diluted samples was assayed by the ELISA. Three dilutions were performed for each sample and the percentage recovery rates were calculated.

| | | | |
|---|---|---|---|
| Mean value (ng/ml) | 591.6 | 157.5 | 179.4 |
| Average % Recovery | 99.1 | 107.5 | 104.6 |
| Range of % Recovery | 90.6-108.2 | 106.3-107.2 | 92.3-111.6 |

The analytical recovery of Hepcidin was estimated at 3 different concentrations in serum samples. Increasing amounts of unlabeled Hepcidin (50 ng/ml, 250 ng/ml, 500 ng/ml) were added to the samples with various initial Hepcidin concentrations. Each sample (non spiked and spiked) was assayed. The Hepcidin concentrations were measured and the percentage recovery rates were calculated.

| | | | |
|---|---|---|---|
| Mean value (ng/ml) | 273.8 | 116.8 | 82.3 |
| Average % Recovery | 93.1 | 94.7 | 97.1 |
| Range of % Recovery | 91.8-94.3 | 89.2-98.7 | 94.5-105.7 |

The intra-assay precision (within-run) variation was determined by repeated measurements (n=12) of 3 control samples with different Hepcidin contents.

Sample 1: mean=426.7; SD=20.2; CV (%)=4.69

Sample 2: mean=210.7; SD=8.58; CV (%)=4.07

Sample 3: mean=110.7; SD=4.74; CV (%)=4.28

The inter-assay precision (between-run) variation was determined by repeated (n=23) measurement (3×) of 3 different control samples in three different kit lots.

Sample 1: mean=431.96; SD=20.8; CV (%)=4.82

Sample 2: mean=216.17; SD=14.44; CV (%)=6.68

Sample 3: mean=109.8; SD=10.72; CV (%)=9.76.

Example 2

Expression of Hepcidin in the Human Kidney
Hepcidin is Expressed in Distal Renal Tubuli and Released into the Urine It is widely believed that iron homeostasis is mainly controlled in the gastrointestinal tract by absorption of dietary iron. However, recent studies show that the kidneys are also involved in iron metabolism. Since the iron regulatory and antimicrobial peptide hepcidin was originally isolated from human urine, Applicants investigated the cellular and subcellular localization of hepcidin in the mammalian kidney and developed an ELISA assay to analyze pro-hepcidin concentrations in serum and urine.

The expression and cellular localization of hepcidin was shown by RT-PCR, Western blot, and immunocytochemistry in human, mouse, and rat kidney with hepcidin specific polyclonal antisera. Its serum and urine concentrations were determined by a sensitive ELISA.

Hepcidin is expressed in human, mouse, and rat kidney. Western blot analysis with region-specific antisera identified a ~9.5 kDa peptide corresponding to the apparent molecular mass of prohepcidin. Localization studies revealed that hepcidin is expressed in the distal tubuli of renal cortex and renal outer medulla. At the subcellular level, hepcidin is localized to the apical membrane domain of secretory tubuli cells which, based on its additional presence in the urine, is obviously released apically into the urine. Enhanced levels of pro-hepcidin (156.8 ng/ml, healthy volunteers 104.2 ng/ml) were determined in patients with CRI indicating that kidneys may metabolize and/or eliminate the circulating hormone.

From the expression of hepcidin in the mammalian kidney, Applicants conclude that the iron regulatory hormone hepcidin is an intrinsic renal peptide, which is not only eliminated/metabolized by the kidney, but also synthesized in the kidney tubule system and released luminally into the urine. Localization of hepcidin in the kidney implicates a regulatory role for this peptide in the renal tubule system.

Introduction

Recent studies have found abnormal hepcidin expression (Muckenthaler et al., (2003) Nat Genet, 34:102-107) and disrupted hepcidin regulation (Bridle et al., (2003) Lancet, 361:669-673; and Kulaksiz et al., (2003) Gut, in press) in HFE-associated hemochromatosis and association of hepcidin mutations with severe juvenile hemochromatosis (Roetto et al., (2003) Nat Genet, 33:21-22). Based on these observations, it has been suggested that hepcidin is a key component of iron homeostasis that act as a negative regulator of iron absorption in the small intestine and iron release from macrophages (Nicolas et al. (2002) Proc Natl Acad Sci USA 99, 4596-4601).

While the majority of studies concentrate on the regulation and function of hepcidin in the liver, the major site of hepcidin production (Park et al.; Kulaksiz et al., (2003) Gut, in press), indications accumulate that this peptide may also play a role in the kidney and urinary tract (Id., Wareing et al., (2003) Am J Physiol Renal Physiol, Epub ahead of print; and Ferguson et al., (2003) Kidney Int, 64:1755-1764). It is widely believed that iron homeostasis is mainly controlled in the gastrointestinal tract at the level of uptake from the diet. The current dogma is that there is no excretory route for iron in the organism. However, recent studies have shown that the kidney plays an important role in iron homeostasis (Wareing et al., (2003) Am J Physiol Renal Physiol, Epub ahead of print; Ferguson et al., (2003) Kidney Int, 64:1755-1764; and Gunshin et al., (1997) Nature, 388:482-488); a significant proportion of iron in serum is available for ultrafiltration by the glomerulus and the majority of iron filtered at the glomerulus is reabsorbed (Wareing et al., (2000) J Physiol, 524.2:581-586).

Hence, it is reasonable to analyze whether hepcidin is also present in the kidney as a local peptide. Therefore, Applicants have raised antisera against various epitopes of the hepcidin precursor molecule and investigated three mammalian species at transcriptional and translational level. Our findings indicate that, beside the elimination of serum hepcidin in the kidney, the peptide is also produced as an intrinsic hormone in the distal tubuli cells of the mammalian kidney and released luminally into the urine, implicating a regulatory role for hepcidin in the kidney and/or urinary tract.

Materials and Methods

TISSUES AND TISSUE PREPARATION: Human kidney samples (n=5) used in the present study were obtained after kidney resection in adult patients with hypernephroma. Human liver samples (n=7) used in the present study were obtained after hemi-hepatectomy in adult patients with liver metastases (Kulaksiz et al., (2003) Gut, in press). Healthy tissues were fixed in 4% paraformaldehyde or in Bouin's fixative for immunohistochemistry or immediately frozen in liquid nitrogen for RT-PCR and Western blot. Rats (n=5) and mice (n=5) were anesthetized and subsequently sacrificed by cervical dislocation. Tissue specimens from kidney and liver were resected and immediately frozen in liquid nitrogen for RT-PCR or Western blot analysis or fixed in paraformaldehyde.

PEPTIDE SYNTHESIS, IMMUNIZATION PROCEDURE, AND ANTIBODIES: From the published pro-hepcidin sequence (Krause et al., (2000) FEBS Lett, 480:147-150; Pigeon et al., (2001) J Biol Chem, 276:7811-7819), the peptides hepcidin-(28-47) and hepcidin-(70-84) were synthesized as C terminal amides using a standard Fmoc protocol (Kulaksiz et al., (2002) Proc Natl Acad Sci USA, 99:6796-6801; and Kulaksiz et al., (2002) Am J Pathol, 161:655-664). Peptides were coupled to keyhole limpet hemocyanin using m-maleimidobenzoyl-N-hydroxysuccinimide ester, and two SPF rabbits (Charles River-Iffa Credo) were immunized with each peptide conjugate (Eurogentec, Seraing, Belgium). The antibodies EG(1)-HepC, EG(2)-HepC [each directed against prohepcidin-(70-84)], and EG(1)-HepN and EG(2)-HepN [each directed against prohepcidin-(28-47)] have been generated, characterized, and used (Kulaksiz et al., (2003) Gut, in press).

EXPRESSION ANALYSES IN THE KIDNEY: Based on the GenBank cDNA sequences, the following primers were constructed and used: human hepcidin (database accession number NM021175) given in 5'-3' orientation, 5'-CTG CAA CCC CAG GAC AGA G-3' and 5'-GGA ATA AAT AAG GA CCC AGG GG-3'; rat hepcidin (# NM 053469), 5'-ACA GAA GGC AAG ATG GCA CT-3' and 5'-GAA GTT GGT GTC TCG CTT CC-3', mouse hepcidin1 (# NM 032541), 5'-CGA TAC CAA TGC AGA AGA GAA GG-3' and 5'-TTC AAG GTC ATT GGT GGG GA-3'. The primers displayed no homology to any previous reported sequences.

RNA isolation was performed using Qiagen RNAeasy kit including DNA digestion. Reverse transcription (RT)-PCR analysis was performed as described previously (Kulaksiz et al., (2002) Proc Natl Acad Sci USA, 99:6796-6801; and Kulaksiz et al., (2002) Am J Pathol, 161:655-664). After an initial denaturation of 94° C. for 4 min, reactions were subjected to 30 cycles of the following thermal program: 94° C. for 30 s, 60° C. for 30 s, and 72° C. for 30 5; this program was followed by a final 5-mm elongation step at 72° C. Amplification products were run on an ethidium bromide-stained 1.8% 89 mE Tris/89 mE boric acid/2 mM EDTA (pH 8.3) agarose gel. As control for specificity, the amplified PCR-products were sequenced by MWG-Biotech.

IMMUNOBLOT ANALYSIS: Western blot experiments were performed on 16.5% tricine-SDS-polyacrylamide gels. Proteins from human, mouse, and rat kidney and liver, as well as from human urine (50 ml for each experiment) were extracted according to the protocols published (Kulaksiz et al., (2003) Gut, in press; Kulaksiz et al., (2002) Proc Natl Acad Sci USA, 99:6796-6801; and Kulaksiz et al., (2002) Am J Pathol, 161:655-664). Following electrophoresis, proteins were transferred onto hydrophobic polyvinylidene fluoride-based membranes (Pall, Portsmouth, England) by semidry blotting. The membranes were incubated overnight with hepcidin antibodies diluted 1:1000. After washing in Tris-buffered saline containing 10 mM Tris-HCl (pH 8.0), 150 mM NaCl, and 0.05% Tween 20, immunoreactive proteins were visualized after incubation with alkaline phosphatase-conjugated goat anti-rabbit antibody (diluted 1:50,000; Sigma) using nitro blue tetrazolium and 5-bromo-4-chloro-3-indolyl phosphate as chromogens (Sigma). The immunoreaction on the Western blot was specifically blocked after preincubation of the antibodies with the corresponding peptide immunogens. Crossreactivity with the second goat anti-rabbit antibody was excluded by appropriate controls (Kulaksiz et al., (2002) Proc Natl Acad Sci USA, 99:6796-6801; and Kulaksiz et al., (2002) Am J Pathol, 161:655-664).

IMMUNOCYTOCHEMICAL PROTOCOL: Tissues were fixed in 4% paraformaldehyde or in Bouin's fixative for 18 h at 4° C. and embedded in paraffin. Paraffin sections (4-5 μm) were immunostained for hepcidin (antibodies EG(1)-HepN, EG(2)-HepN, EG(1)-HepC, and EG(2)-HepC, each diluted 1:2000) by the avidin-biotin-peroxidase complex (ABC) technique; the incubation sequences and the visualization of the antigen-antibody binding sites were performed as detailed (Kulaksiz et al., (2003) Gut, in press; Kulaksiz et al., (2002) Proc Natl Acad Sci USA, 99:6796-6801; and Kulaksiz et al., (2002) Am J Pathol, 161:655-664). In brief, the sections were incubated with the respective antibodies for 24 h at 4° C., followed by incubation with biotinylated anti-rabbit IgG (Jackson Immunoresearch, West Grove, Pa., USA) for 30 min diluted 1:200. The sections were then incubated for 30 min with a preformed complex of biotin-peroxidase/streptavidin (Jackson Immunoresearch), diluted in PBS (final concentrations: biotin-peroxidase, 0.7 μg/ml; streptavidin, 5 μg/ml). The antigen-antibody binding sites were detected by incubation of the sections in 0.7 mM diaminobenzidine hydrochloride/0.002% $H_2O_2$ in 0.05 M Tris-HCl (pH 7.6).

SPECIFICITY CONTROLS: Method-dependent non-specificities were excluded by running controls as published (Kulaksiz et al., (2003) Gut, in press). Antibody specificities were tested by preadsorption of the antibodies with homologous and heterologous antigenic peptides (6.25-100 μg/ml of the antiserum) (Kulaksiz et al., (2002) Proc Natl Acad Sci USA, 99:6796-6801; and Kulaksiz et al., (2002) Am J Pathol, 161:655-664). Preadsorption of the antibodies with homologous antigens at concentrations as low as 6.25 μg/ml completely blocked immunostaining in the kidney, while preadsorption of the antibodies with heterologous antigens at concentrations up to 100 μg/ml had no effect on immunostaining.

HEPCIDIN ELISA COMPETITIVE BINDING ASSAY: Serum and urine samples were obtained from 22 individuals (11 women, 11 men, aged 23-59, mean 39 yrs) and serum samples were obtained from 22 patients with renal insufficiency undergoing chronic hemodialysis (11 women, 11 men, aged 25-77 years, mean 48 years). All patients with chronic renal insufficiency were treated 2-3 times a week with 3,000 IE recombinant human erythropoietin (EPO). During sample collection it was taken care that the healthy volunteers and patients had no infection and no bleeding. 10 ml blood samples were withdrawn into serum-tubes and 10 ml urine samples were collected in urine-tubes, centrifuged at 2,500×g for 10 min at 4° C. Determinations were performed in duplicate using 96-well-microtiter plates as described (8). In brief, microtiter plates were coated with 200 μl/well rabbit anti-hepcidin antibody EG(2)-HepN diluted 1:4000. 50 μl standards containing various amounts of synthetic peptides (0, 20, 100, 500, and 1000 ng/ml) or human serum and urine samples and 150 μl N-terminally biotinylated hepcidin-(28-47) (Peptide Specialty Laboratories GnibH, Heidelberg, Germany) (2 ng/well) were added to each well and incubated for 1 hour at RT. After washing with TBST (TBS with 0.05% Tween 20), the biotinylated antigen-antibody complexes were detected by streptavidin-peroxidase enzyme (Dako, Hamburg, Germany) with the substrate tetramethylbenzidine (DRG Instruments GmbH, Marburg, Germany); the color reaction was stopped with 1 M $H_2SO_4$ and the extinction of the solution was read at 450/630 nm wavelength.

STATISTICAL ANALYSIS: Data are illustrated as means±SEM. The statistical analysis was evaluated by Student's t-test. The differences were considered significant at $P<0.05$.

Results

EXPRESSION OF HEPCIDIN IN THE MAMMALIAN KIDNEY: RT-PCR analysis revealed clear expression of hepcidin not only in the liver (positive control, see Kulaksiz et al., (2003) Gut, in press), but also in human, rat and mouse kidney (FIG. 8). A 192-bp expected PCR product for man, a 193-bp product for mouse, 201-bp product for rat were detected in the liver (data not shown) and kidney of these species. The sequence analysis revealed that the PCR-generated products have a complete homology with the cDNAs of the corresponding peptides.

At the translational level, the presence of hepcidin was confirmed by Western blotting studies with region-specific antibodies (FIG. 8). Antisera directed against the C and N terminus of the hepcidin precursor molecule coincidentally identified an immunoreactive band of ~9.5 kDa in extracts of human, rat and mouse kidney.

Figure 9:
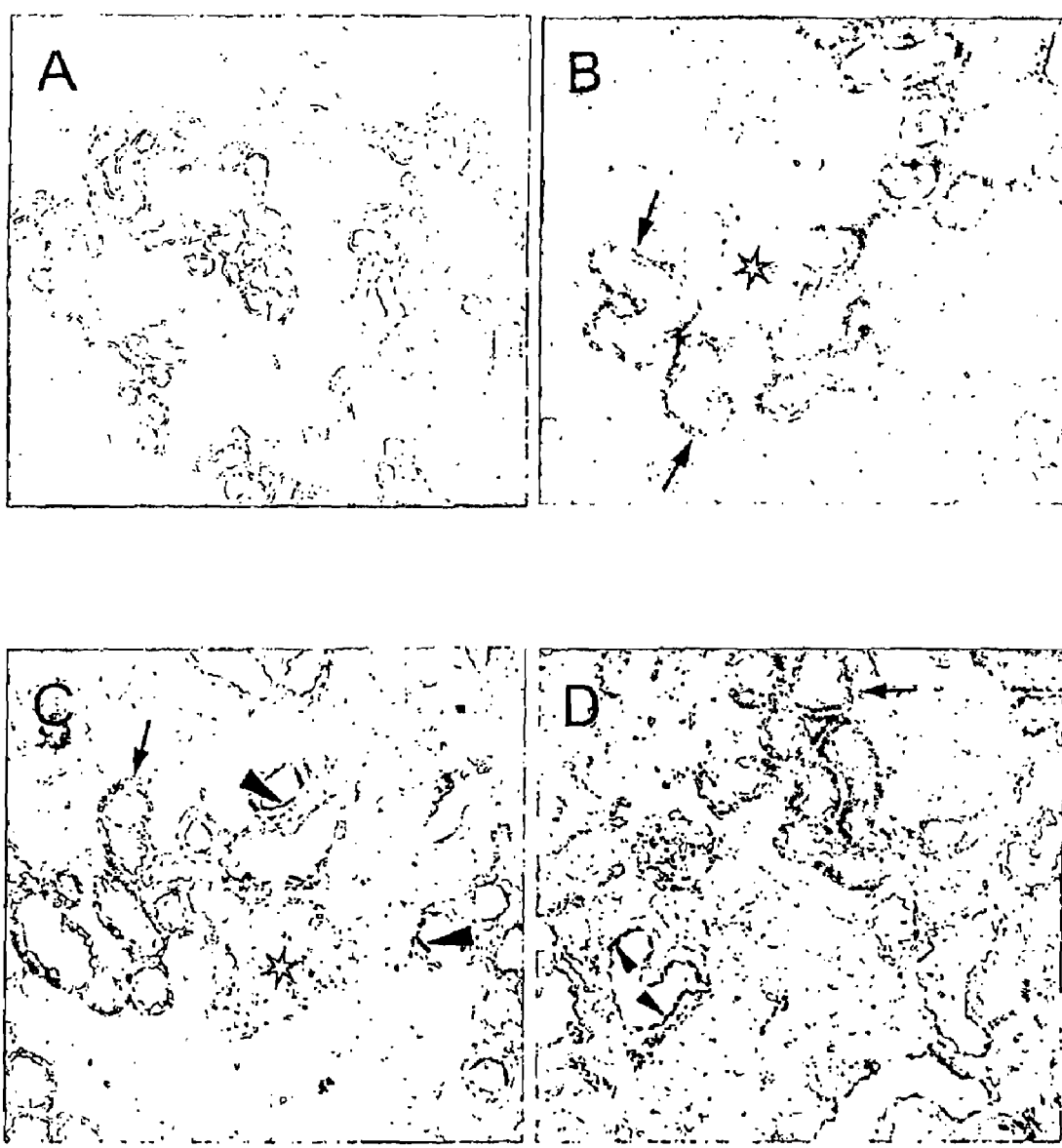
FIG. 9 illustrates the cellular localization of hepcidin in rat renal cortex. The paraffin sections immunostained with the region-specific antibodies EG(1)-HepC (A), EG(2)-HepC (B), EG(1)-HepN (C), and EG(2)-HepN (D) show a distinct immunoreactivity in distal tubuli of the renal cortex. In some tubuli immunoreactivity is distributed within the cytoplasm of the epithelial cells (arrows), but in others the immunoreactivity is localized at the apical pole of the respective cells (D, arrowheads). Note that glomeruli asterisks) lack any hepcidin immunoreactivity. (Magnification: A, ×90; B-D, ×180)
Figure 10:
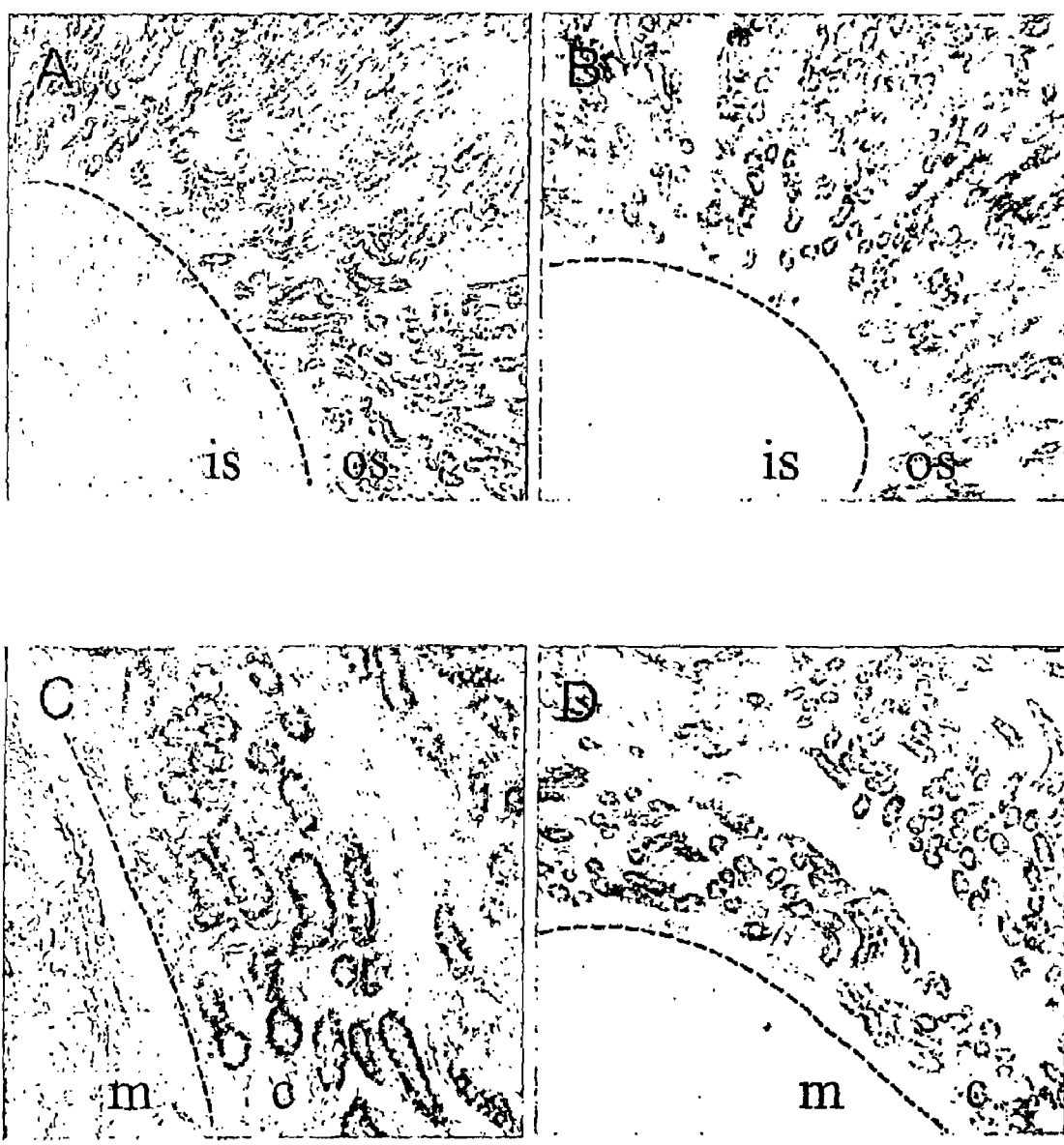
FIG. 10 illustrates the tissue distribution of hepcidin in rat (A and C) and mouse (B and D) kidney. Immunohistochemistry with antibody EG(2)-HepN shows the outer medulla (A and B) with marked decrease of hepcidin immunoreactivity between the outer stripe (os) and inner stripe (is), which is indicated by black dotted arcs. C and D show the lack of hepcidin immunoreactivity in the inner medulla (m). Strong immunoreactivity is observed in the cortex (c). (Magnification: A, B, and D, ×90; C, ×180)
Figure 11:
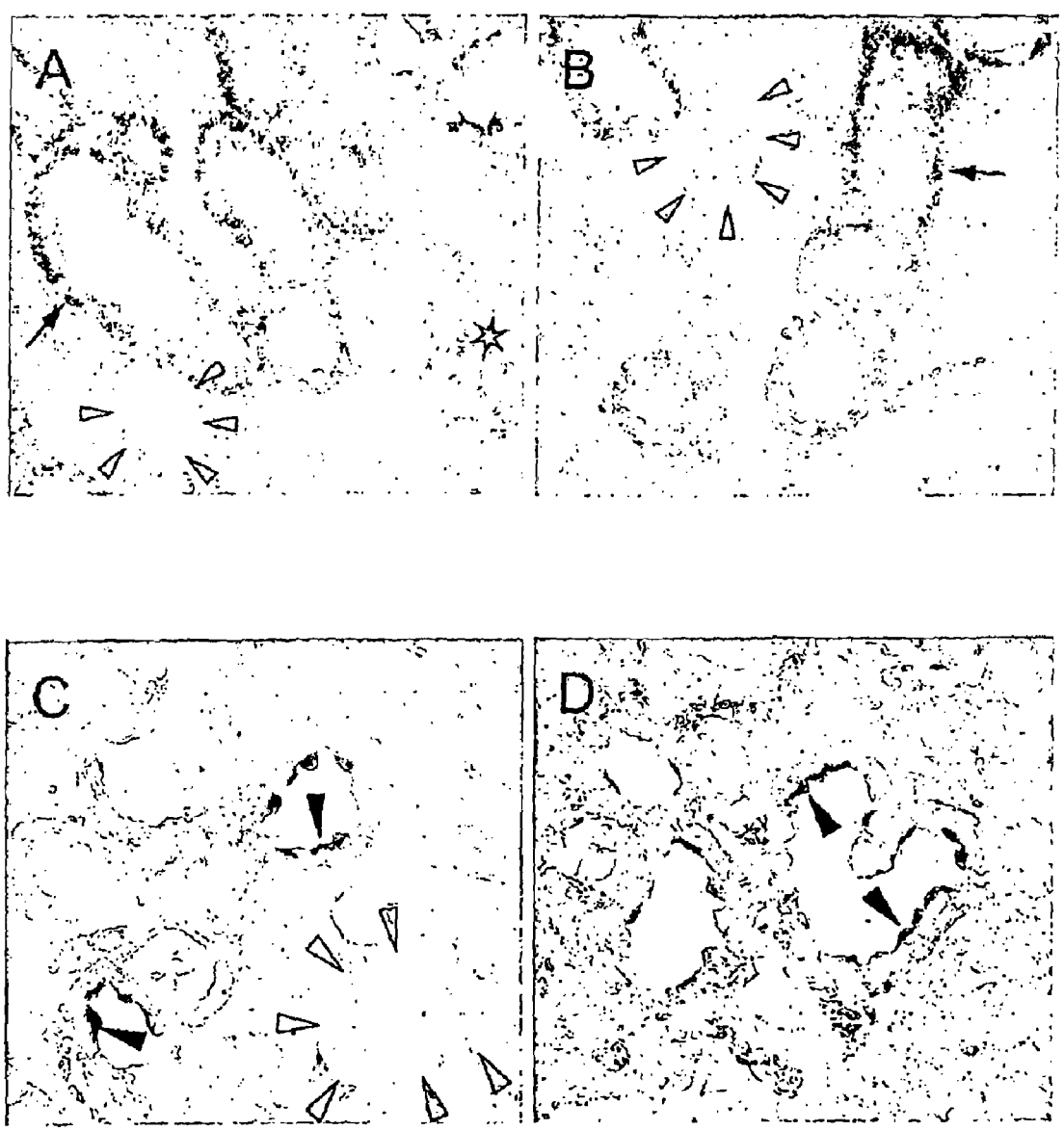
FIG. 11 illustrates the subcellular localization of hepcidin in the rat kidney with antibodies EG(1)-HepN (A), EG(2)-HepN (B and D), and EG(1)-HepC (C). In some distal tubuli hepcidin immunoreactivity is distributed within the cytoplasm of the epithelial cells (arrows), but in others the immunoreactivity is strongly concentrated toward the apical pole of the respective cells (black arrowheads). Note that glomeruli (asterisk) and proximal tubuli (transparent arrowheads) lack any hepcidin immunoreactivity. (Magnification: A-D, ×360)
Figure 13:
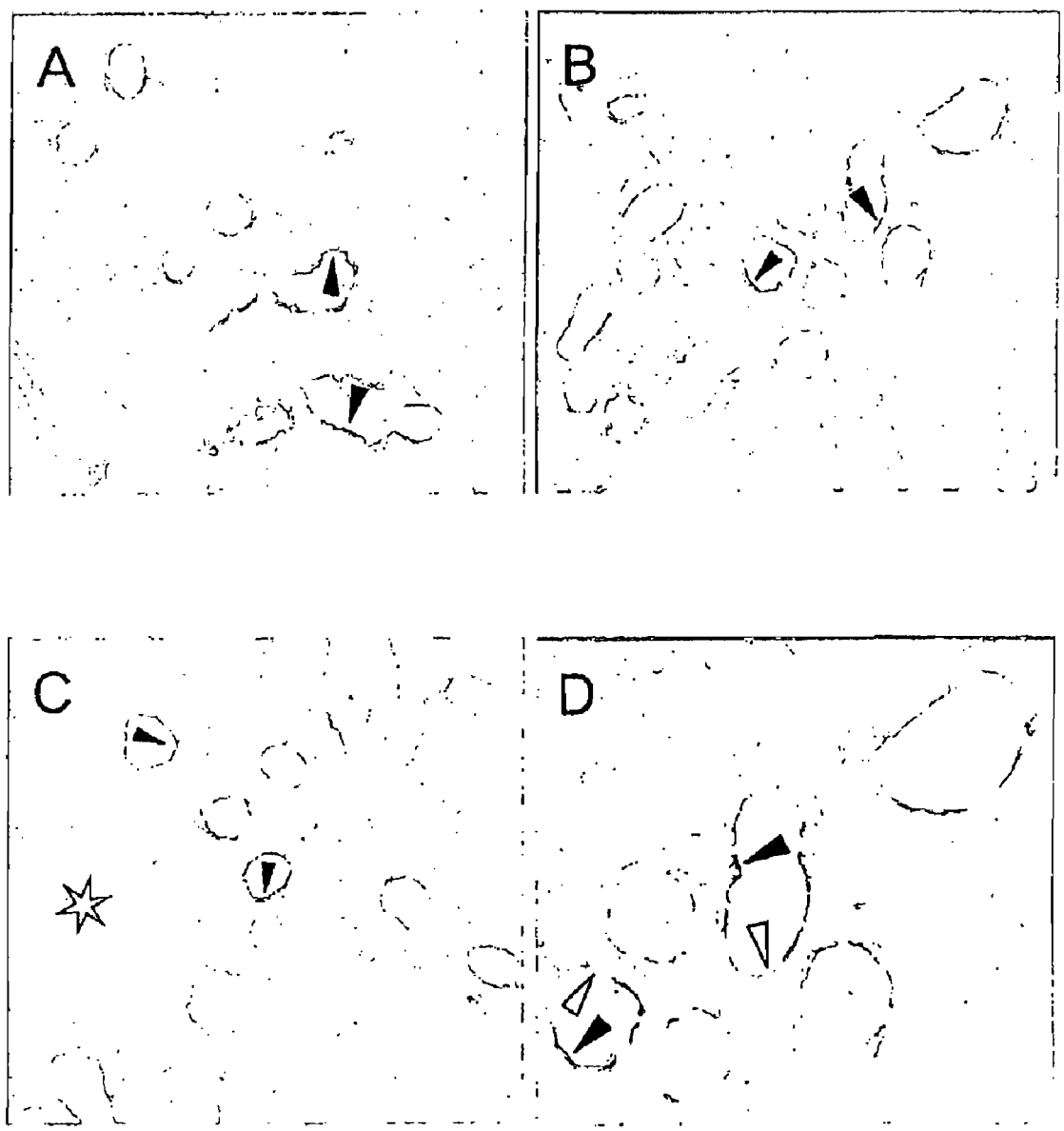
FIG. 13 illustrates the detection of hepcidin immunoreactivity at the apical pole of distal tubuli cells in human kidney with antibodies EG(1)-HepN (A), EG(2)-HepN (B and D), and EG(2)-Hep C(C). Note the strong immunostaining at the apical pole of the secretory epithelial cells (black arrowheads, some cells lack hepcidin immunoreactivity (transparent arrowheads). The asterisk indicate a glomerulus. (Magnification: A-C, ×180; 0, ×360)

CELLULAR LOCALIZATION OF HEPCIDIN: Immunohistochemical studies with region-specific hepcidin antisera consistently localized hepcidin to the distal tubulus system of the human, mouse and rat kidney (FIGS. 9-13). The proximal renal tubuli, collecting tubuli, and the glomeruli completely lacked hepcidin immunoreactivity. The immunoreactive dital tubuli were confined to the renal cortex and outer renal medulla, the inner renal medulla showed no immunostaining for hepcidin (FIGS. 9, 10). Notably, distinct intercellular differences exist between the hepcidin positive tubuli cells: while the majority of tubuli cells was strongly positive for hepcidin, some of them showed only a faint immunoreactivity or were totally unreactive for hepcidin (FIG. 12). Conspicuously, in all sections investigated, the hepcidin antisera revealed a granular immunoreactivity pattern in the cytoplasm of epithelial cells lining the distal tubuli (FIGS. 9, 10). In some tissues, hepcidin-positive cells showed strong immunoreactivity concentrated at the apical pole of the secretory cells (FIGS. 11, 13), and no immunoreactivity was found at the basolateral membrane domain of the respective cells.

Figure 14:
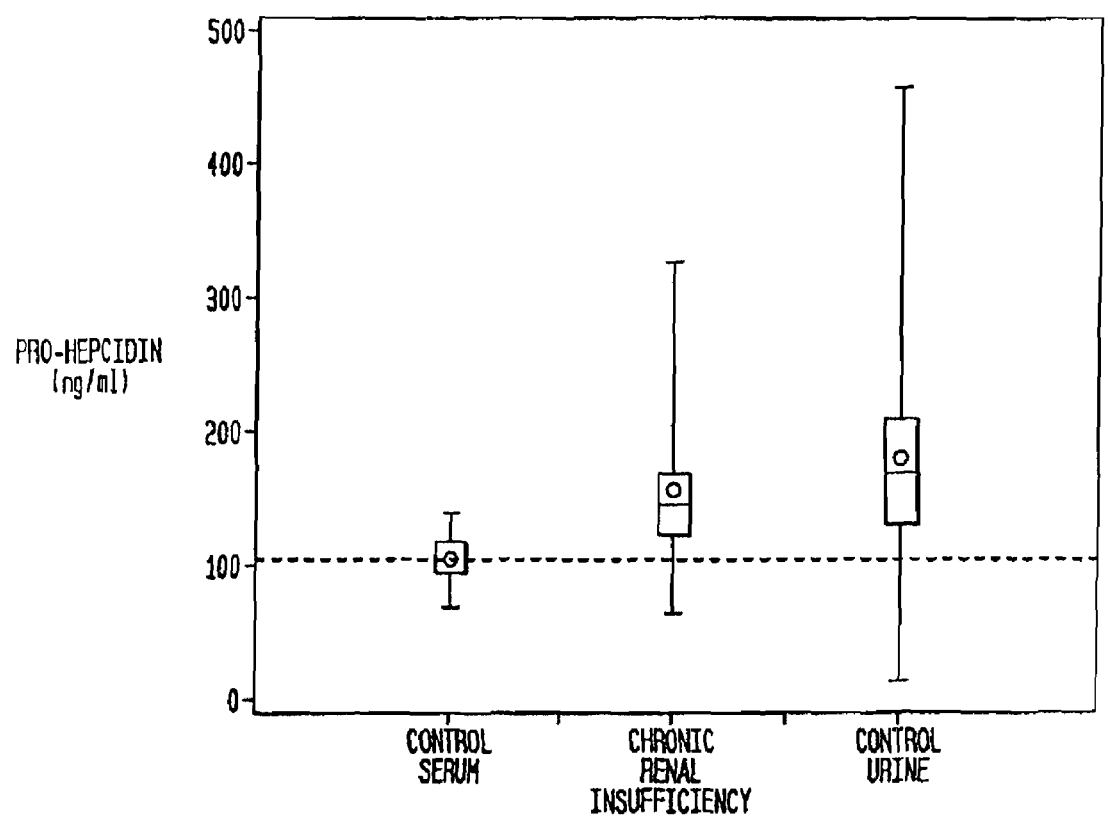
FIG. 14 illustrates box-plot of values of venous serum and urine pro-hepcidin concentrations in 22 healthy volunteers (control) and 22 patients with chronic renal insufficiency. The line within the box indicates the median, and the circle indicates the mean. The lower and upper edge of the box indicates the 1st and 3rd quartile, the whiskers the minimum and maximum values. The dashed line marks the mean level of the control group for circulating immunoreactive pro-hepcidin (104.2 ng/ml).

DETECTION OF HEPCIDIN PROPEPTIDE IN SERUM AND URINE: A stable hepcidin ELISA assay with high reproducibility and sensitivity was developed with the specific N-terminal hepcidin antibody EG(2)-HepN (Kulaksiz et al., (2003) Gut, in press). As seen in FIG. 14, the ELISA revealed that pro-hepcidin is present in human serum. Pro25 hepcidin was measured in the range from 68.5 to 139.2 ng/ml (mean±SE; 104.2±19.5 ng/ml) in the serum of healthy subjects. The prohepcidin concentrations varied from 63.9 to 327.3 ng/ml (mean±SE; 156.8±61.9 ng/ml) in the serum of patients suffering from chronic renal insufficiency and were significantly increased compared with that in control group.

Using the sensitive hepcidin ELISA, pro-hepcidin was detected in human urine from the control group in the range from 13.9 to 456.0 ng/ml (mean±SE; 180.1±94.8 ng/ml). The presence of prohepcidin in human urine was also confirmed by Western blotting analysis. Hepcidin antisera identified in extracts of human urine a single hepcidin immunoreactive band of ~9.5 kDa molecular mass that comigrated exactly with the immunoreactive hepcidin in kidney tissues (FIG. 8)

Discussion

The new hormone hepcidin is an antimicrobial peptide and a central regulator of iron homeostasis (Park et al., (2001) J Bid Chem, 276:7806-7810; Krause et al., (2000) FEBS Lett, 480:147-150; Pigeon et al., (2001) J Biol Chem, 276:7811-7819; Nicolas et al., (2001) Proc Natl Acad Sci USA, 98:8780-8785; and Nicolas et al., (2002) Proc Natl Acad Sci USA, 99:4596-4601). In previous studies, it was shown that the liver is the main source of hepcidin (Park et al., CH (2001) J Bid Chem, 276:7806-7810; and Kulaksiz et al., (2003) Gut, in press). Although hepcidin was originally isolated from human urine (Park et al., (2001) and hemofiltrate (Krause et al., (2000)), no expression of this regulatory peptide was detected in the kidney (Pigeon et al., (2001).

Using the appropriate primer specifications and combinations successfully employed in the liver (Kulaksiz et al., (2003) Gut, in press; and Gehrke et al., (2003) Blood, 102: 371-376), the present RT-PCR analysis clearly revealed that hepcidin is not only expressed in the liver, but also in the kidney of three mammalian species—man, rat and mouse. Sequencing analysis revealed the specificity of the generated PCR-products.

To verify the presence of the translated hepcidin peptide in the kidney, Applicants raised a bulk of region-specific antisera against hepcidin and used them in Western blotting analyses and immunohistochemistry. Western blot analysis confirmed expression of hepcidin in the kidney. Four different antisera recognizing different epitopes in the hepcidin precursor molecule concurrently identified an immunoreactive peptide of ~9.5 kDa in the kidney of three different species, which corresponds to the molecular mass of hepcidin prohormone deduced from the respective cDNA sequence (Pigeon et al., (2001)). The apparent molecular mass of this immunoreactive peptide is also in accordance with the molecular mass of hepcidin prohormone detected in the liver (Kulaksiz et al., (2003) Gut, in press). Applicants' findings unequivocaly demonstrated that hepcidin is not liver specific, since it is also present in the kidney.

Immunocytochemical investigations with four region-specific hepcidin antisera revealed that in human, mouse, and rat kidney, hepcidin is specifically localized to the tubule system of the renal cortex and outer medulla. These immunoreactive tubules were identified as distal renal tubuli by their typical morphological feature detected in light microscopy. Coincident staining by different region-specific antibodies not only in the human, but also in mouse and rat kidney points to distal tubuli being the source of renal hepcidin. No immunoreactivity for hepcidin was detected in the proximal renal tubuli, collecting tubuli, and the glomeruli or the renal inner medulla.

In the renal cortex and outer medulla, hepcidin immunoreactivity was confined to epithelial secretory cells of the distal tubuli. Remarkably, all hepcidin antisera produced a granular immunoreactivity pattern assuming localization of the peptide in small secretory vesicles or lysosomes of the respective cells that have been already identified in these cells by electron microscopy (van Katachalan M A, Kritz W: Pathology of the kidney. Edited by J C Jennette, J L Oldson, M M Schwarz, S G Silver: Philadelphia, Heptinstall's, 1998, pp 3-66). Notably, distinct intercellular differences exist between the epithelial cells even of the same tubulus with respect to the density of hepcidin immunoreactivity that may reflect intercellular differences in expression or secretion of hepcidin. Conspicuously, in some tubuli immunoreactivity for hepcidin was localized in the whole cytoplasm of the epithelial cells whereas in other tubuli strong hepcidin immunoreactivity was concentrated at the apical pole of the secretory cells. This peculiar distribution pattern of hepcidin at the cellular level may assume a luminally directed release of hepcidin. Applicants did not detect hepcidin expression at the basolateral membrane domain of renal tubuli cells. This suggests that renal hepcidin is not released into the blood by secretory cells lining the tubuli.

It is widely believed that control of iron homeostasis of the body is mainly dependent on tight regulation of iron uptake from the diet in the proximal small intestine. However, recent studies have shown that the kidney plays an important role in iron homeostasis (Wareing et al., (2003) Am J Physiol Renal Physiol, Epub ahead of print; Ferguson et al., (2003) Kidney mt1 64:1755-1764; and Gunshin et al., (1997) Nature, 388: 482-488). Wareing and co-workers could convincingly demonstrate that a metabolically significant amount of iron is filtered at the glomerulus and only 0.8-1.5% of the filtered iron is actually excreted in the urine (Wareing et al., (2000) J Physiol, 524.2:581-586). Thus, there must be a very effective pathway and a strong regulation for reabsorption of iron along the renal tubules. Indeed, Ferguson and co-workers could localize the divalent metal transporter 1 (DMT-1) in the tubule system of the kidney (Ferguson et al., (2001) Am J Physiol Renal Physiol, 280:F803-F814). This protein is proposed to be the major pathway for uptake of dietary iron by the gastrointestinal tract (Gunshin et al., (1997)). Notably, DMT-1 expression has been shown to be highest at the apical membrane domaine of the tubuli cells of renal cortex and outer medulla, where Applicants also found hepcidin. Furthermore, recent studies demonstrated that altered dietary iron intake strongly modulates renal DMT-1 expression (Wareing et al., (2003)). Based on these findings and data showing that hepcidin expression inversely correlates with the expression of duodenal DMT-1 (Frazer et al., (2002) Gastroenterology, 123:835-844), Applicants suggest a regulatory role for hepcidin in renal iron transport.

The potential release of hepcidin into the urine was substantiated by Western blot studies. The region-specific hepcidin-antisera coincidentally identified a strongly labeled band of correct molecular mass (Kulaksiz et al., (2003) Gut, in press) that co-migrated exactly with the immunoreactive pro-hepcidin as in kidney tissue extracts. These findings clearly show that prohepcidin is synthesized by secretory distal tubuli cells and released luminally into the urine where it apparently escapes tubular proteolysis and recycling. To measure the prohepcidin concentration in human urine, a sensitive ELISA with a detection sensitivity of 3.95 ng/well was developed. ELISA analyses with the hepcidin antiserum EG(2)-HepN, which was already successfully used in ELISA experiments (Kulaksiz et al., (2003) Gut, in press) revealed a high concentration of prohepcidin in the range from 13.9 to 456.0 ng/ml (mean±SE; 180.1±94.8 ng/ml) in urine of healthy subjects. This concentration is considerably higher than the prohepcidin concentration of the same persons in the circulation (68.5 to 139.2 ng/ml; mean±SE, 104.2±19.5 ng/ml). Notably, no correlation was found between the circulating pro-hepcidin and the serum iron or ferritin levels (ICulaksiz et al., (2003) Gut, in press). Likewise, no correlation was detected between urinary prohepcidin and serum iron or ferritin levels (data not shown), that are supposed to regulate the expression of liver hepcidin (Pigeon et al., (2001) J Biol Chem, 276:7811-7819; Nemeth et al., (2002 Blood, 101: 2461-2463; and Ganz T, (2003) Blood, 102:783-788). Therefore, Applicants suggest that the regulation of renal/urinary pro-hepcidin is not directly influenced by serum iron or ferritin.

The evaluation of pro-hepcidin regulation in renal insufficient patients undergoing chronic hemodialysis revealed that concentrations of pro-hepcidin in the serum of these patients were significantly increased from 104.2 ng/ml in healthy subjects to 156.8 ng/ml. Enhanced levels of pro-hepcidin in dialysis patients suggests that the kidneys are not only involved in the synthesis of hepcidin, but they may also be involved in the metabolism and/or elimination of the circulating peptide. Interestingly, in a current study the kidney hormone erythropoietin has been shown to down-regulate the liver hepcidin gene expression (Nicolas (2002) Blood Cells, Molecules, and Diseases, 29:327-335). Thus, another explanation for the enhanced pro-hepcidin concentrations in dialysis patients could be the relative deficiency of erythropoietin, which is encountered regularly in terminal renal insufficiency (Eckardt K U, (2000) Clin Nephrol, 53:S2-8; and Santoro A: (2002) Rev din Exp Hematol, Suppi 1:12-20). However, Applicants report enhanced levels of pro-hepcidin measured in patients with chronic renal insufficiency, although they were treated with the hepcidin inhibitory hormone erythropoietin, supporting the renal filtration of hepcidin. One embodiment of the present invention provides that urinary hepcidin originates partly from the kidney and partly from the liver; therefore, it has to be noticed that the measured urinary pro-hepcidin is a total of released renal peptide and the eliminated circulating peptide.

Summing up, recent studies demonstrate that the kidney plays an important role in iron homeostasis (Wareing et al., (2003) Am J Physiol Renal Physiol, Epub ahead of print; Ferguson et al., (2003) Kidney Int, 64:1755-1764; Gunshin et al., (1997) Nature, 388:482-488; Wareing et al., (2000) J Physiol, 524.2:581-586 and Ferguson et al., (2001) Am J Physiol Renal Physiol, 280:F803-F814), however, no data exists about the regulatory mechanism of the renal iron transport. In this respect, Applicants localized hepcidin for the first time in the kidney of three mammalian species. Applicants' findings indicate that hepcidin is not liver-specific. Beside the elimination of serum hepcidin in the kidney, the peptide is also produced as an intrinsic hormone in the secretory distal tubuli cells of the kidney and released luminally into the urine, implicating a regulatory role for hepcidin in the kidney and/or urinary tract. Further studies should analyze the regulatory mechanism of hepcidin in the renal tubule system.

Example 3

Expression of Hepcidin in the Human Pancreas

Pancreatic tissues used in the present study were obtained after the Whipple operation in patients suffering from pancreatic cancer. Using the appropriate primer specifications and combinations successfully employed in the liver and kidney, the present RT-PCR analysis revealed that hepcidin is not only expressed in the liver and kidney, but also in the human pancreas. Sequencing analysis revealed the specificity of the generated PCR products.

Western blot analyses with specific antibodies confirmed the expression of hepcidin in the pancreas at the translational level. Using the same antibodies, hepcidin was localized in the pancreas by immunohistochemistry. Paraffin sections revealed that hepcidin immunoreactivity is localized in the endocrine pancreas; no immunoreactivity was found in the exocrine pancreas.

INDUSTRIAL APPLICABILITY

The invention has applications in connection with diagnosing a disease condition characterized by non-physiological levels of hepcidin protein, including prohepcidin and fragments thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

The invention claimed is:

1. A method of detecting hepcidin comprising the steps of:
(a) obtaining a tissue or fluid sample from a subject; and (b) contacting the sample with an antibody or fragment thereof that specifically binds to one or more carboxy terminal epitopes contained within amino acids 70 to 84 of SEQ ID NO: 2; wherein the tissue or fluid sample is selected from the group consisting of a kidney sample, a liver sample, and a urine sample, and wherein the method of detecting hepcidin is selected from the group consisting of Western blot, immunodot, immunohistochemistry, and immunofluorescence.

2. The method of claim 1, wherein said hepcidin is hepcidin, prohepcidin or fragments thereof.

3. The method of claim 1, wherein said hepcidin is prohepcidin.

* * * * *

SEQUENCE LISTING

```
<160> NUMBER OF SEQ ID NOS: 8

<210> SEQ ID NO 1
<211> LENGTH: 391
<212> TYPE: DNA
<213> ORGANISM: Homo sapiens

<400> SEQUENCE: 1
tcaagaccca gcagtgggac agccagacag acggcacgat ggcactgagc tcccagatct      60
gggccgcttg cctcctgctc ctcctcctcc tcgccagcct gaccagtggc tctgttttcc     120
cacaacagac gggacaactt gcagagctgc aaccccagga cagagctgga gccagggcca     180
gctggatgcc catgttccag aggcgaagga ggcgagacac ccacttcccc atctgcattt     240
tctgctgcgg ctgctgtcat cgatcaaagt gtgggatgtg ctgcaagacg tagaacctac     300
ctgccctgcc cccgtcccct cccttcctta tttattcctg ctgccccaga acataggtct     360
tggaataaaa tggctggttc ttttgttttc c                                    391

<210> SEQ ID NO 2
<211> LENGTH: 84
<212> TYPE: PRT
<213> ORGANISM: Homo sapiens

<400> SEQUENCE: 2

Met Ala Leu Ser Ser Gln Ile Trp Ala Ala Cys Leu Leu Leu Leu Leu
  1               5                  10                  15

Leu Leu Ala Ser Leu Thr Ser Gly Ser Val Phe Pro Gln Gln Thr Gly
```

```
                    20                  25                  30

Gln Leu Ala Glu Leu Gln Pro Gln Asp Arg Ala Gly Ala Arg Ala Ser
        35                  40                  45

Trp Met Pro Met Phe Gln Arg Arg Arg Arg Asp Thr His Phe Pro
    50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 3
<211> LENGTH: 20
<212> TYPE: PRT
<213> ORGANISM: Homo sapiens

<400> SEQUENCE: 3

Pro Gln Gln Thr Gly Gln Leu Ala Glu Leu Gln Pro Gln Asp Arg Ala
1               5                   10                  15

Gly Ala Arg Ala
            20

<210> SEQ ID NO 4
<211> LENGTH: 15
<212> TYPE: PRT
<213> ORGANISM: Homo sapiens

<400> SEQUENCE: 4

Cys Gly Cys Cys His Arg Ser Lys Cys Gly Met Cys Cys Lys Thr
1               5                   10                  15

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
ctgcaacccc aggacagag                                              19

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
ggaataaata aggaagggag ggg                                         23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gattcagggt cagggaggtg                                             20

<210> SEQ ID NO 8
<211> LENGTH: 20
<212> TYPE: DNA
<213> ORGANISM: Artificial Sequence
```

```
-continued

<220> FEATURE:
<223> OTHER INFORMATION: Description of Artificial Sequence: Primer

<400> SEQUENCE: 8
gaaggggctg tgattgaagg                                              20
```